(12) United States Patent
Wang et al.

(10) Patent No.: US 6,831,089 B2
(45) Date of Patent: Dec. 14, 2004

(54) MUSCARINIC ANTAGONISTS

(75) Inventors: Yuguang Wang, East Brunswick, NJ (US); Samuel Chackalamannil, East Brunswick, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/266,505

(22) Filed: Oct. 8, 2002

(65) Prior Publication Data

US 2003/0207917 A1 Nov. 6, 2003

Related U.S. Application Data

(60) Provisional application No. 60/328,356, filed on Oct. 10, 2001.

(51) Int. Cl.$^7$ ..................... A61K 31/445; C07D 401/04
(52) U.S. Cl. ...................... 514/316; 514/314; 514/318; 546/168; 546/186; 546/189; 546/191
(58) Field of Search ................................. 514/314, 316, 514/318; 546/168, 186, 189, 191, 193

(56) References Cited

U.S. PATENT DOCUMENTS

| 6,294,554 B1 | 9/2001 | McComble et al. | ........ | 514/316 |
| 6,602,885 B2 * | 8/2003 | Baroudy et al. | ............ | 514/316 |

FOREIGN PATENT DOCUMENTS

| WO | WO 98/05292 | 2/1998 |

OTHER PUBLICATIONS

Baroudy et al. "Preparation of piperidine derivatives as CCR5 antagonists" CA 136:369611 (2002).*
Miyasawa et al. "Optically active compounds . . . " Ca 128:134484 (1998).*
Copy of International Search Report for PCT/US/ 02/32199 dated Oct. 8, 2002—5 Pages.
Logemann et al., "Influence of Dichloroacetylation on the Antimicrobial Activity of Chloramphenicol Derivatives and of Various Amines," Brit. J. Pharmacology. 17:286–296 (1961).
Melchiorre et al., "Synthesis and Biological Activity of Some Methoctramine–Related Tetraamines Bearing a 11–Acetyl–5,11–dihydro–6H–pyrido[2,3–b][1,4]–benzodiazepin–6–one Moiety as Antimuscarinics: A Second Generation of Highly Selective $M_2$ Muscarinic Receptor Antagonists" J. Med. Chem. 36:3734–3737 (1993).
Baumgold et al., "3–α–Chlorimperialine: an $M_2$ –selective muscarinic receptor antagonist that penetrates into brain" Eur. J. Pharmacol. 251:315–317 (1994).

* cited by examiner

Primary Examiner—Celia Chang
(74) Attorney, Agent, or Firm—William Y. Lee

(57) ABSTRACT

The present invention discloses compounds, which are novel muscarinic receptor antagonists, as well as methods for preparing such compounds. In another embodiment, the invention discloses pharmaceutical compositions comprising such muscarinic receptor antagonists as well as methods for using them to treat cognitive disorders such as Alzheimer's disease.

15 Claims, No Drawings

MUSCARINIC ANTAGONISTS

CROSS REFERENCE TO RELATED APPLICATIONS

This application claims the benefit of U.S. Provisional Application No. 60/328,356 filed on Oct. 10, 2001.

FIELD OF THE INVENTION

The present invention relates to compounds useful in the treatment of cognitive disorders, pharmaceutical compositions containing the compounds, methods of treatment using said compounds of the present invention, and to the use of said compounds in combination with acetylcholinesterase inhibitors.

BACKGROUND OF INVENTION

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize M2 muscarinic receptors, especially in relation to M1 muscarinic receptors, should possess activity against cognitive disorders. Baumgold et al. (Eur. J. of Pharmacol., 251, (1994) 315–317) disclose 3-α-chloroimperialine as a highly selective M2 muscarinic antagonist.

The present invention is predicated on the discovery of a class of 1,4-di-substituted piperidines, some of which have M2 selectivity even higher than that of 3-α-chloroimperialine. Logemann et al (Brit. J. Pharmacol. (1961), 17, 286–296) describe certain di-N-substituted piperazines, but these are different from the compounds of the present invention. Furthermore, the compounds of Logemann et al. are not disclosed to have activity against cognitive disorders.

SUMMARY OF THE INVENTION

In one aspect, the present application provides a compound having the general structure shown in Formula I:

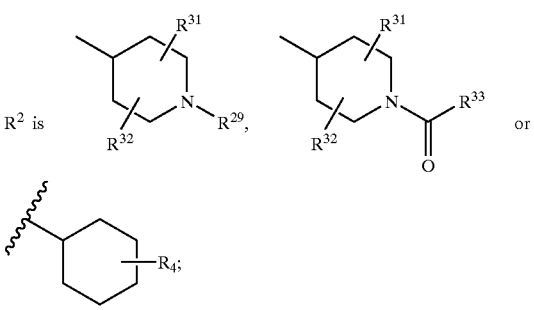

or a pharmaceutically acceptable salt or solvate of said compound, wherein:

Z is N, C(H), or C-(alkyl);

X is —O—, —S—, —SO—, —S(O)$_2$—, —C(O)—, —CH$_2$—, or —C(S);

R is 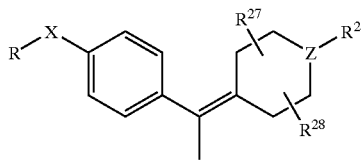

$R^2$ is 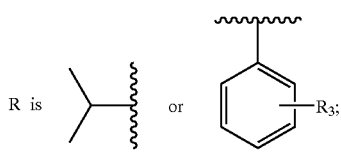

$R^3$ is 1 to 5 substituents which can be the same or different, each said substituent being either alkoxy or halo;

$R^4$ is hydrogen or 1 to 3 substituents which can be the same or different, each said substituent being either alkyl or haloalkyl;

$R^{27}$ is hydrogen or 1 or 2 subsitutents which can be the same or different, each said substituent being independently selected from the group consisting of alkyl, hydroxyalkyl, arylalkyl, aminoalkyl, haloalkyl, alkylthio, alkylthioalkylene, carboxyalkyl, imidazolyalkyl and indolyalkyl;

$R^{28}$ is hydrogen or 1 or 2 subsitutents which can be the same or different, each said substituent being independently selected from the group consisting of alkyl, hydroxyalkyl, arylalkyl, aminoalkyl, haloalkyl, alkylthio, alkylthioalkylene, carboxyalkyl, imidazolyalkyl and indolyalkyl; or $R^{27}$ and $R^{28}$ can be joined together to form an alkylene group;

$R^{29}$ is hydrogen, alkyl, —C(O)-alkyl, —C(O)-cycloalkyl, alkoxycarbonyl, aminocarbonyl, aryloxycarbonyl, alkylaminocarbonyl, alkylsulfonyl, arysulfonyl or —SO$_2$—NH—$R^{35}$;

$R^{31}$ is hydrogen or 1 or 2 subsitutents which can be the same or different, each said substituent being independently selected from the group consisting of alkyl, aryl, cycloalkyl, hydroxyalkyl, aminoalkyl, hydroxy, —N($R^{35}$)$_2$, —O-acyl, —N($R^{35}$)acyl, —OC(O)O$R^{35}$ and —OC(O)N($R^{35}$)$_2$;

$R^{32}$ is hydrogen or 1 or 2 subsitutents which can be the same or different, each said substituent being independently selected from the group consisting of alkyl, aryl, cycloalkyl, hydroxyalkyl, aminoalkyl, hydroxy, —N($R^{35}$)$_2$, —O-acyl, —N($R^{35}$)acyl, —OC(O)O$R^{35}$ and —OC(O)N($R^{35}$)$_2$, or $R^{31}$ and $R^{32}$ can be joined together to form the group —(CH$_2$)$_r$—, wherein r is 1, 2, 3, 4, 5 or 6;

$R^{33}$ is aryl or heteroaryl with the proviso that when $R^{33}$ is heteroaryl, the C(O)—$R^{33}$ bond is to a carbon atom in the $R^{33}$ group;

and $R^{35}$ is hydrogen, aryl or alkyl.

The compound of formula I can be useful as M2 muscarinic receptor antagonists and can be useful in the treatment of Alzheimer's disease and other neurodegenerative or cognitive diseases. Another embodiment of this invention is directed to pharmaceutical compositions for the treatment of neurodegenerative or cognitive diseases. The compositions comprise a disease- or disorder-treating amount of a compound of formula I, or a pharmaceutically acceptable salt of said compound, and a pharmaceutically acceptable carrier therefor.

DETAILED DESCRIPTION

In one embodiment, the present invention provides compounds which are represented by structural formula I, or a pharmaceutically acceptable salt or solvate thereof. In one preferred embodiment of formula I,

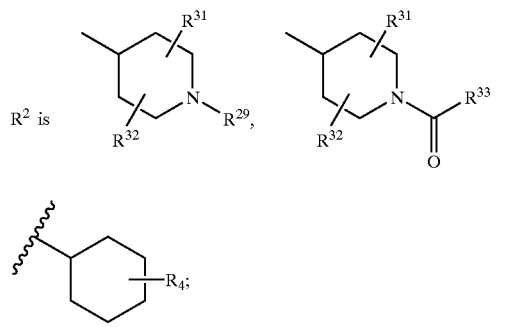

and

X —O—, —S—, —SO— or —S(O)$_2$—, or a pharmaceutically acceptable salt or solvate of the compound.

In a preferred embodiment of formula I, R$^2$ and X are defined as follows:

TABLE 1

| No. from table of compounds | R$^2$ | X |
|---|---|---|
| 1 | (4-piperidinyl)-N-C(O)-(4,7-difluoronaphthalen-1-yl) | O |
| 2 | (4-piperidinyl)-N-C(O)-(4,5-difluoronaphthalen-1-yl) | O |
| 3 | (4-piperidinyl)-N-C(O)-(4,5-difluoronaphthalen-1-yl) | S |
| 4 | (4-piperidinyl)-N-C(O)-(4,7-difluoronaphthalen-1-yl) | S |
| 5 | (4-piperidinyl)-N-C(O)-(2,3-dichlorophenyl) | SO |
| 6 | (4-piperidinyl)-N-C(O)-(2,3-dichlorophenyl) | S |
| 7 | 4-piperidinyl (NH) | S |
| 8 | 4-piperidinyl (NH) | O |
| 9 | (4-piperidinyl)-N-C(O)-(2-amino-3-chlorophenyl) | O |

TABLE 1-continued

| No. from table of compounds | R² | X |
|---|---|---|
| 10 | 4-piperidinyl-N-C(=O)-(2,3-dichlorophenyl) | O |
| 11 | 4-piperidinyl-N-C(=O)-(4-fluoronaphth-1-yl) | S |
| 12 | 4-piperidinyl-N-C(=O)-(naphth-1-yl) | S |
| 13 | 4-piperidinyl-N-C(=O)-(4-fluoronaphth-1-yl) | SO₂ |
| 14 | 4-piperidinyl-N-C(=O)-(naphth-1-yl) | SO₂ |
| 15 | 4-piperidinyl-N-C(=O)-(quinolin-5-yl) | S |
| 16 | 4-piperidinyl-N-C(=O)-(6-ethoxynaphth-1-yl) | S |
| 17 | 4-piperidinyl-N-C(=O)-(quinolin-5-yl) | SO |
| 18 | 4-piperidinyl-N-C(=O)-(6-ethoxynaphth-1-yl) | SO₂ |
| 19 | 4-piperidinyl-N-C(=O)-(6-ethoxynaphth-1-yl) | SO |
| 20 | 4-piperidinyl-N-C(=O)-(2-amino-3-methylphenyl) | SO₂ |

TABLE 1-continued

| No. from table of compounds | R² | X |
|---|---|---|
| 21 | 4-piperidinyl-N-C(O)-(2-amino-3-methylphenyl) | SO |
| 22 | 4-piperidinyl-N-C(O)-(2-amino-3-methylphenyl) | S |
| 23 | 4-piperidinyl-N-C(O)-(2-methoxy-3-methylphenyl) | S |
| 24 | 4-piperidinyl-N-C(O)-(2-methoxy-3-methylphenyl) | $SO_2$ |
| 25 | 4-piperidinyl-N-C(O)-(2-methoxy-3-methylphenyl) | SO |
| 26 | 4-piperidinyl-N-C(O)-(3-fluoro-7-indolyl) | S |
| 27 | 4-piperidinyl-N-C(O)-(7-benzimidazolyl) | S |
| 28 | 4-piperidinyl-N-C(O)-(3-fluoro-7-indolyl) | $SO_2$ |
| 29 | 4-piperidinyl-N-C(O)-(3-fluoro-7-indolyl) | SO |
| 30 | 4-piperidinyl-N-C(O)-(7-benzimidazolyl) | $SO_2$ |
| 31 | 4-piperidinyl-N-C(O)-(7-benzimidazolyl) | SO |

TABLE 1-continued
| No. from table of compounds | R² | X |
|---|---|---|
| 32 | 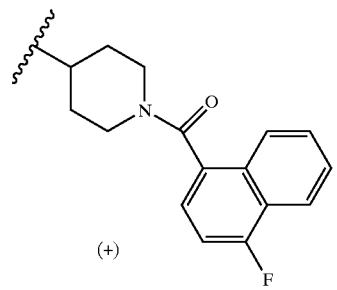 (+) | SO |
| 33 | 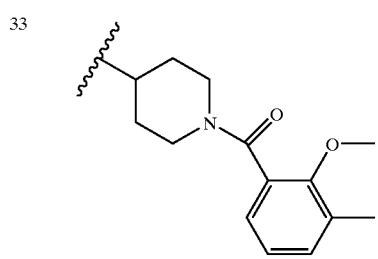 | SO |
| 34 | 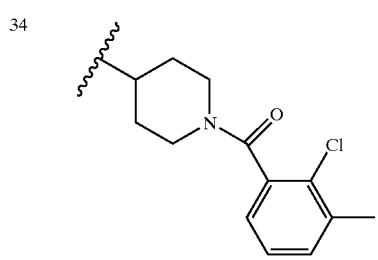 | SO₂ |
| 35 | 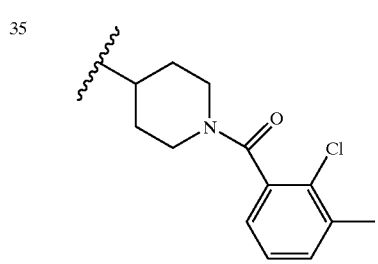 | SO |
| 36 | 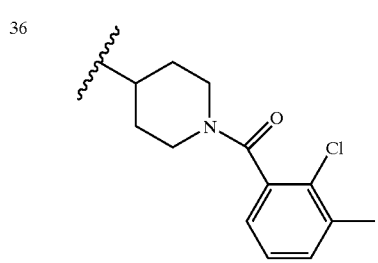 | S |
| 37 | 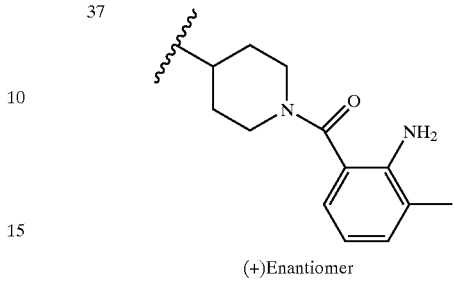 (+)Enantiomer | SO |
| 38 | 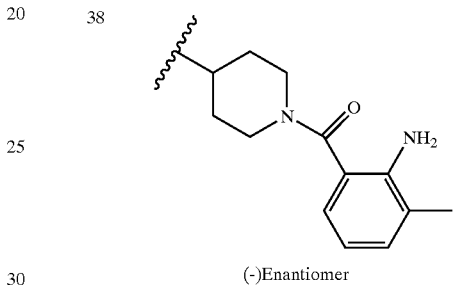 (−)Enantiomer | SO |
| 39 | 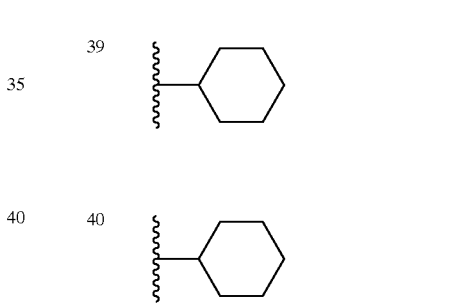 | O |
| 40 | 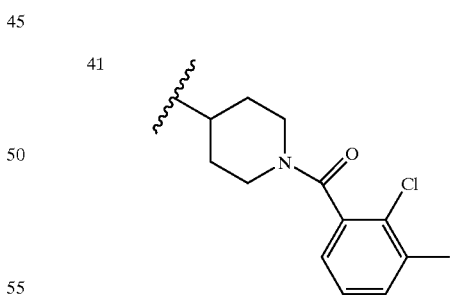 | S |
| 41 | 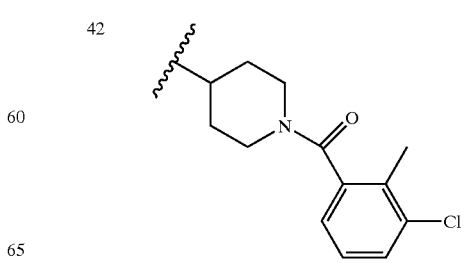 | O |
| 42 | 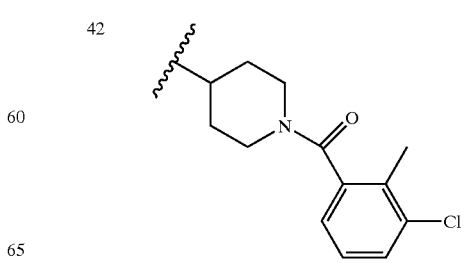 | O |

TABLE 1-continued

| No. from table of compounds | R² | X |
|---|---|---|
| 43 | 4-(2-amino-3-methylbenzoyl)piperidin-4-yl | O |
| 44 | cyclohexyl | SO₂ |
| 45 | cyclohexyl | SO |
| 46 | 4-isopropylcyclohexyl | S |
| 47 | 4-(trifluoromethyl)cyclohexyl | S |
| 48 | 1-(3-chloro-2-methylbenzoyl)piperidin-4-yl | S |
| 49 | 4-methylcyclohexyl | SO₂ |
| 50 | 4-methylcyclohexyl | SO |
| 51 | 3-methylcyclohexyl | SO₂ |
| 52 | 3-methylcyclohexyl | SO |
| 53 | 1-(3-chloro-2-methylbenzoyl)piperidin-4-yl | SO₂ |
| 54 | 1-(3-chloro-2-methylbenzoyl)piperidin-4-yl | SO |
| 55 | 4-isopropylcyclohexyl | SO₂ |
| 56 | 4-isopropylcyclohexyl | SO |
| 57 | 1-(3-chlorobenzoyl)piperidin-4-yl | SO |
| 58 | 1-(2,3-dichlorobenzoyl)piperidin-4-yl | SO |
| 59 | trans-3-methylcyclohexyl | O |
| 60 | trans-3-methylcyclohexyl | S |

TABLE 1-continued

| No. from table of compounds | R² | X |
|---|---|---|
| 61 | (trans-4-methylcyclohexyl) | S |
| 62 | (trans-3-methylcyclohexyl) | SO |
| 63 | (1-(3-chlorobenzoyl)piperidin-4-yl) | SO |
| 64 | (1-(2,3-dichlorobenzoyl)piperidin-4-yl) | O |
| 65 | (piperidin-4-yl) | SO |
| 66 | (trans-4-methylcyclohexyl) | SO |
| 67 | (cis-4-methylcyclohexyl) | SO |

In preferred embodiments of formula I, the compound of the present invention has the following formulae, including pharmaceutically acceptable salts or solvates thereof:

[structure]

,

[structure]

or

[structure]

In another preferred embodiment, the compound of the present invention has the following formulae, including pharmaceutically acceptable salts or solvates thereof:

[structure]

[structure] (+)

,

-continued

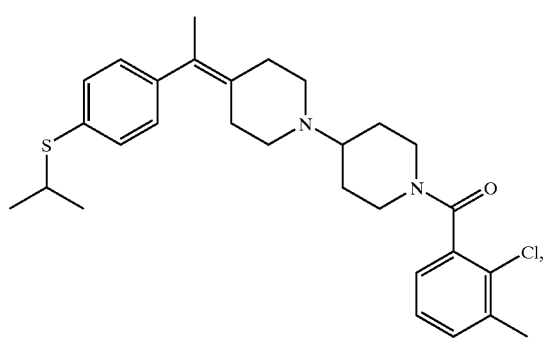

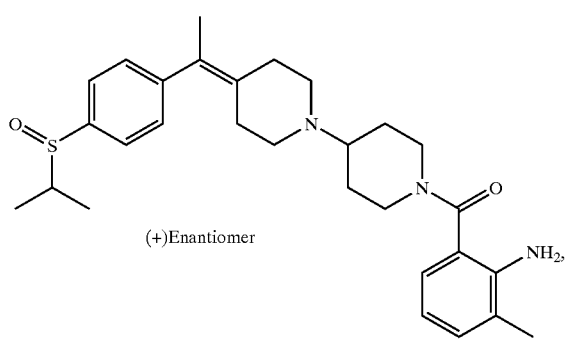

(+)Enantiomer

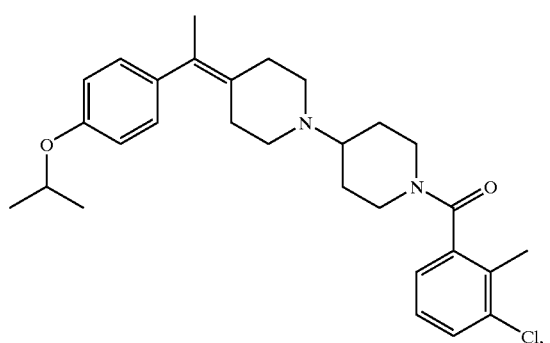

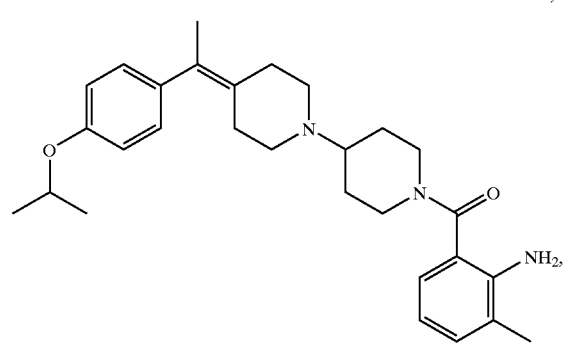

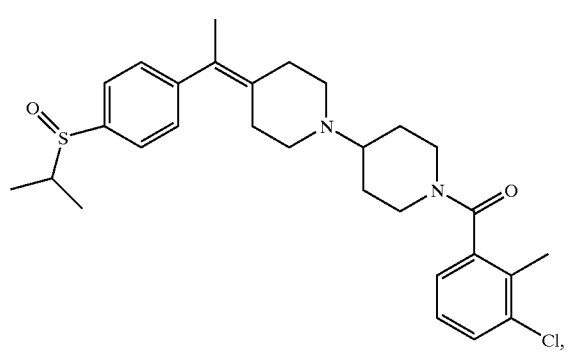

-continued

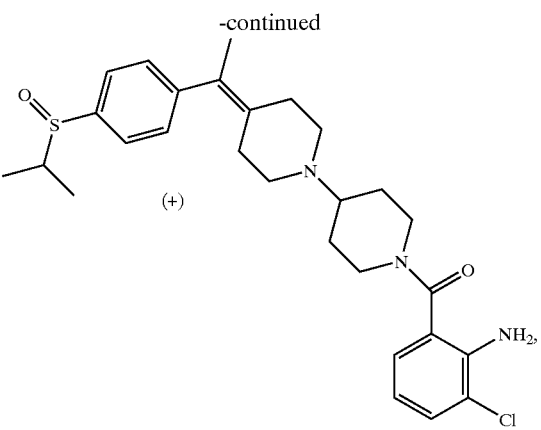

(+)

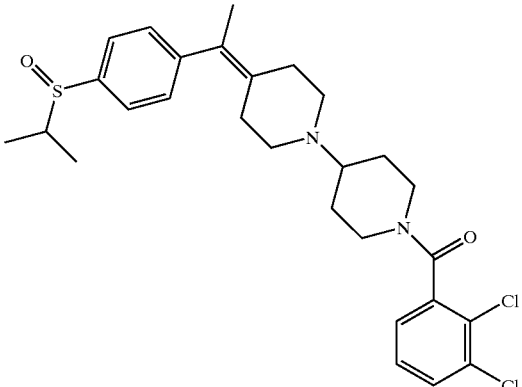

or

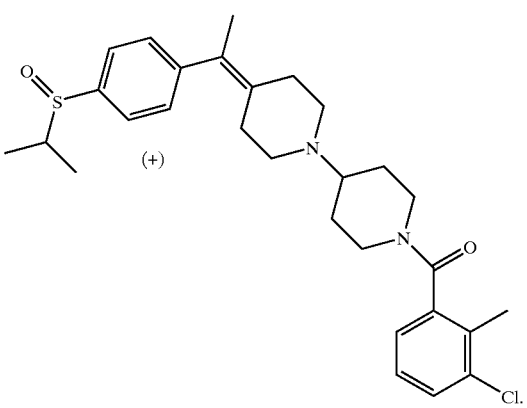

(+)

Except where stated otherwise, the following definitions apply throughout the present specification and claims. These definitions apply regardless of whether a term is used by itself or in combination with other terms. Hence the definition of "alkyl" applies to "alkyl" as well as the "alkyl" portions of "alkoxy", "haloalkyl", etc.

Unless otherwise known, stated or shown to be to the contrary, the point of attachment for a multiple term substituent (multiple terms that are combined to identify a single moiety) to a subject structure is through the last named term of the multiple term. For example, an "arylalkyl" substituent attaches to a targeted structure through the "alkyl" portion of the substituent. Conversely, when the substituent is "alkylaryl", it attaches to a targeted structure through the "aryl" portion of the substituent. Similarly, a cycloalkylalkyl substituent attaches to a targeted through the latter "alkyl" portion of the substituent (e.g., Structure-alkyl-cycloalkyl).

"Patient" includes both human and other mammals.

"Mammal" means humans and other animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, and 2-butynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" means an aromatic monocyclic or multicyclic ring system comprising about 6 to about 14 carbon atoms, preferably about 6 to about 10 carbon atoms. The aryl group can be unsubstituted or optionally substituted on the ring with one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different, each being independently selected from the group consisting of hydrogen, alkyl, aryl, and aralkyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthlenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2-dihydropyridyl, 1,4-dihydropyridyl, 1,2,3,6-tetrahydropyridyl and the like. Non-limiting examples of suitable oxaheterocyclenyl groups include 3,4-dihydro-2H-pyran, dihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from the group consisting of hydrogen, alkyl, aryl, and aralkyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl and the like.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Sulfonyl" means a group of the formula —S(O)$_2$—.

"Sulfinyl" means a group of the formula —S(O)—.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, isopropoxy, and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylamino" means an —NH$_2$ or —NH$_3$+group in which one or more of the hydrogen atoms on the nitrogen is replaced by an alkyl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Alkylthioalkylene" means an alkyl-S-alkyl group in which the alkylene and alkylthio group is as previously described. Non-limiting examples of suitable alkylthioalkyl groups include methylthiomethylene and ethylthioethylene. The bond to the parent moiety is through the alkyl group.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl. "Aminocarbonyl" means an amino-O—C(O)— group. Non-limiting example of a suitable aminocarbonyl group is NH$_2$—O—C(O)—. The bond to the parent moiety is through the carbonyl.

"Alkylaminocarbonyl" means an alkyl-aminocarbonyl group. Non-limiting example of a suitable alkylaminocarbonyl group is methyl-NH—O—C(O)—. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O. In general, the solvated forms, with pharmaceutically acceptable solvents such as water, ethanol and the like, are equivalent to the unsolvated forms for purposes of this invention.

"Effective amount" or "therapeutically effective amount" is meant to describe an amount of compound of the present invention effective binding to muscarinic receptor subtypes and thus producing the desired therapeutic effect.

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

When a variable appears more than once in the structural formula, for example $R^5$ when X is —$C(OR^5)_2$—, the identity of each variable appearing more than once may be independently selected from the definition for that variable.

The individual isomers can be prepared using conventional resolution procedures, e.g., treatment with an appropriate optically active acid, separating the diastereomers and then recovering the desired isomer. In addition, the individual optical isomers may be prepared by asymmetric synthesis.

Also, in the case of an acid (—COOH) or alcohol group being present, pharmaceutically acceptable esters can be employed such as methyl, ethyl, butyl, acetate, maleate, pivaloyloxymethyl, and the like, and those esters know in the art for modifying solubility or hydrolysis characteristics for use as sustained release or prodrug formulations.

In one embodiment, the present invention provides a pharmaceutical composition which comprises a compound of structural formula I in combination with a pharmaceutically acceptable carrier.

In another embodiment, the present invention provides a method of making a pharmaceutical composition comprising mixing a compound of formula I with a pharmaceutically acceptable carrier.

Another aspect of the invention relates to a method of treating a cognitive or neurodegenerative disease comprising administering to a patient suffering from said disease an effective amount of a compound of formula I.

Another aspect of the invention relates to a method of treating a cognitive or neurodegenerative disease comprising administering to a patient suffering from said disease an effective amount of a combination of a compound of formula I with an acetylcholinesterase inhibitor.

Another aspect of the invention relates to a kit for treating a cognitive or neurodegenerative disease comprising in separate containers in a single package pharmaceutical compounds for use in combination, in one container an acetylcholine release enhancing compound of formula I and in a second container an acetycholinesterase inhibitor, said compound and inhibitor each being in a pharmaceutically acceptable carrier and their combined quantities being an effective amount.

The compounds of formula I exhibit selective M2 and/or M4 muscarinic antagonizing activity, which has been correlated with pharmaceutical activity for treating cognitive disorders such as Alzheimers disease and senile dementia.

For combination treatment with more than one active agent, where the active agents are in separate dosage formulations, the active agents may be administered separately or in conjunction. In addition, the administration of one element may be prior to, concurrent to, or subsequent to the administration of the other agent.

For preparing pharmaceutical compositions, one or more active compounds are admixed with pharmaceutically acceptable, inert carriers. Active compounds include, but are not limited to, the compound of the present invention, compounds capable of enhancing ACh release, and ACh'ase inhibitors. The pharmaceutically acceptable carriers may be either solid or liquid.

Solid form preparations include powders, tablets, dispersible granules, capsules, cachets and suppositories. A solid carrier can be one or more substances which may also act as dilutents, flavoring agents, solubilizers, lubricants, suspending agents, binders or tablet disintegrating agents; it may also be an encapsulating material. Liquid form preparations include solutions, suspensions and emulsions. As an example may be mentioned water or water-propylene glycol solutions for parenteral injection.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The compound of the present invention, or pharmaceutical compositions thereof, may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides addition, fatty acids such as oleic acid find use in the preparation of injectables.

The compound of the present invention, or pharmaceutical compositions thereof, may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compound of the present invention, or pharmaceutical compositions thereof, can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compound of the present invention, or pharmaceutical compositions thereof, may also be delivered as a suppository employing bases such as cocoa butter, glycerinated gelatin, hydrogenated vegetable oils, mixtures of polyethylene glycols of various molecular weights and fatty acid esters of polyethylene glycol.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The quantity of active compound in a unit dose preparation may be varied or adjusted from 1 mg to 100 mg according to the particular application and the potency of the active ingredient and the intended treatment. This would correspond to a dose of about 0.001 to about 20 mg/kg which may be divided over 1 to 3 administrations per day. The composition may, if desired, also contain other therapeutic agents.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

When a compound of formula I or a compound capable of enhancing ACh release is used in combination with an acetylcholinesterase inhibitor to treat cognitive disorders, these two active components may be co-administered simultaneously or sequentially, or a single pharmaceutical composition comprising a compound of formula I or a compound capable of enhancing ACh release and an acetylcholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the acetylcholinesterase inhibitor may range from 0.001 to 100 mg/kg body weight.

Another aspect of the invention relates to a method of treating a cognitive or neurodegenerative disease comprising administering to a patient suffering from said disease an affective amount of a compound of the present invention.

Another aspect of the invention relates to a method of treating a cognitive or neurodegenerative disease comprising administering to a patient suffering from said disease an effective amount of a combination of a compound of the present invention with an acetylcholinesterase inhibitor.

Another aspect of the invention relates to a method of treating a cognitive or neurodegenerative disease comprising administering to a patient suffering from said disease an effective amount of a combination of an acetylcholine release enhancing compound with an acetylcholinesterase inhibitor. The acetylcholinesterase inhibitor is preferably an M2 or M4 selective muscarinic antagonist.

Another aspect of the invention relates to a kit for treating a cognitive or neurodegenerative disease. The kit comprises separate containers for which their contents are to be combined, wherein one container contains an acetylcholine release enhancing compound and a separate container contains an acetycholinesterase inhibitor. The compound and inhibitor are each in a pharmaceutically acceptable carrier and their combined quantities are an effective amount. The acetylcholine release enhancing compound is preferably an M2 or M4 selective muscarinic antagonist.

The invention disclosed herein is exemplified by the following preparation and examples which should not be construed to limit the scope of the disclosure. Alternative mechanistic pathways and analogous structures may be apparent to those skilled in the art.

EXAMPLE 1

Synthesis of Compound Nos. 41, 47, 48, 61 and 62

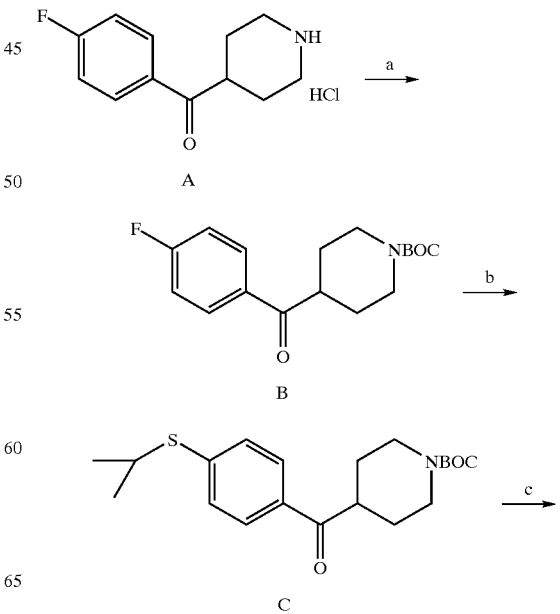

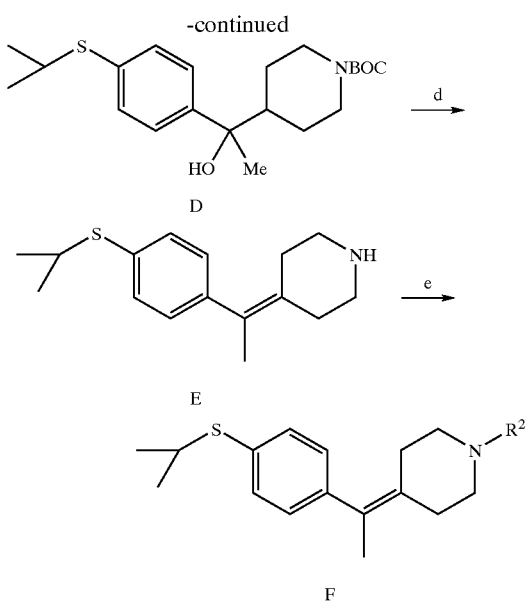

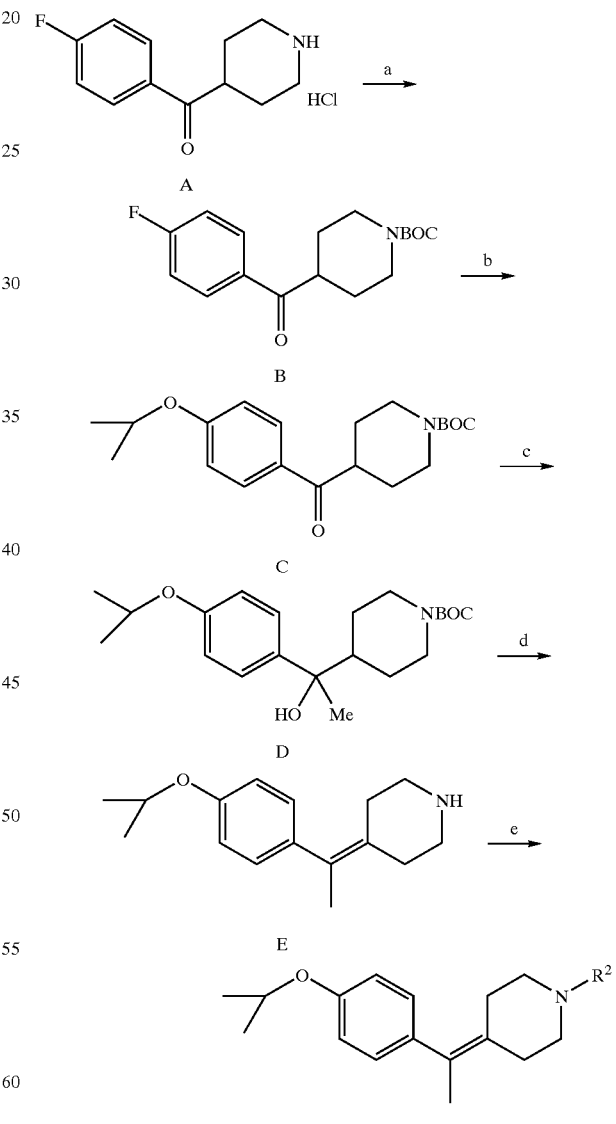

Step A: Commercially available 4(4-Fluorobenzyl) piperidine hydrochloride (25 g, 0.1026 mol) was dissolved and mixed in a solution containing 10% diethylether (126 ml) and 10% NaOH (126 ml). The mixture was cooled down to 0° C., and a solution of Di-t-butyl dicarbonate (26.88 g, 0.1231 mol) in $Et_2O$ (50 ml) was added dropwise. The mixture was stirred at room temperature overnight, then extracted with $Et_2O$ (3×200 ml). The organic layers were combined, dried over $MgSO_4$, and evaporated to dryness to afford compound B (30.7 g, 97%).

Step B: Sodium hydride (4.92 g, 0.123 mol, 60% in oil dispersion) was suspended in DMF (50 ml) followed by addition of 2-propanethiol (9.06 ml, 0.0976 mol) at 0° C. under $N_2$. After the reaction mixture was stirred at room temperature for 5 minutes, compound B (15 g, 0.0488 mol) was added portionwise. The reaction mixture was heated to 65° C. for 6 hrs and then cooled down to room temperature. After 200 ml of 1N NaOH solution was added to the mixture, it was stirred for 3 days to let excess 2-propanethiol oxidized. The reaction mixture was then extracted with $Et_2O$ (3×300 ml). The combined $Et_2O$ phase was dried over $NaHCO_3$ and evaporated. Compound C was re-crystallized from $Et_2O$ (15.8 g, 89%).

Step C: Compound C (15 g, 0.4126 mol) was dissolved in THF (80 ml). After the solution was cooled down to −78° C., methyl lithium solution (1.5M in ethyl ether, 41.26 ml, 0.0619 mol) was added dropwise. The reaction mixture was stirred at room temperature under $N_2$ for 1 hr. Saturated $NaHCO_3$ solution (200 ml) was added to the reaction mixture followed by extraction with $CH_2Cl_2$ (3×200 ml). The combined organic phase was dried over $MgSO_4$ and evaporated. Compound D was obtained (15 g, 95%).

Step D: Compound D (8.0 g, 0.0211 mol) was dissolved in $CH_2Cl_2$ (25 ml) and trifluoroacetic acid (25 ml) was added. The reaction mixture was refluxed overnight and then cooled to room temperature. The reaction mixture was then diluted with 1N NaOH solution (100 ml). The mixture was extracted with $CH_2Cl_2$ (2×100 ml). The combined organic phase was dried over $NaHCO_3$ and evaporated. Compound E was obtained (5.33 g, 96%).

Step E: Sodium triacetoxyborohyide (12.98 g, 0.061 mol) was added to a solution of compound E (5.33 g, 0.02 mol) and 0.03 mol of the appropriate ketone in dichloroethane (100 ml). The ketones that were used to synthesize compounds 41, 47, 48, 61 and 62 were, respectively, cyclohexone, 4-n-propylcyclohexone, cyclohexone, 4-trifluoromethylcylcohexone, and 3-methylcyclohexone for compounds 61 and 62. These ketones added on to compound E to create the $R^2$ group of compound F. $R^2$ has the same meaning as described above in Table 1. The reaction mixture was stirred under $N_2$ at room temperature overnight, then quenched by 1N NaOH solution (200 ml). The reaction mixture was extracted with $CH_2Cl_2$ (3×200 ml). The combined organic phase was dried over $NaHCO_3$ and evaporated. The residue was purified by flash column chromatography (20% EtOAc in Hexane) to afford compound F (9.22 g).

EXAMPLE 2

Synthesis of Compound Nos. 41, 47, 48, 61 and 62

The same procedure as described in Example 1 was used except that 2-propanol was substituted for 2-propanethiol in Step B. The ketones that were used in Step E to make Compound Nos. 40 and 60 were, respectively, cyclohexone and 3-methylcyclohexone.

EXAMPLE 3

Synthesis of Compound No. 7

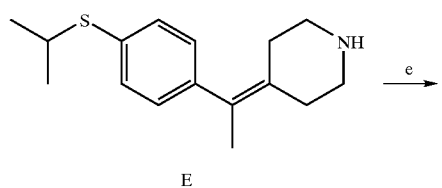

E

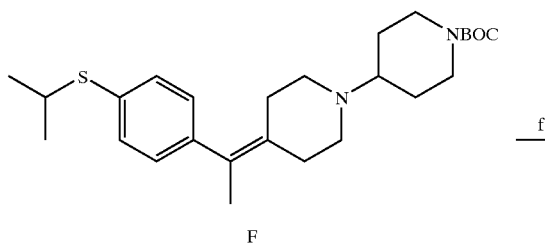

F

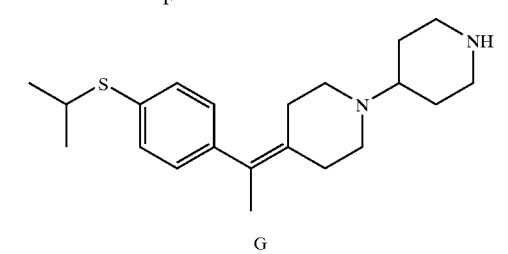

G

The same procedure as described in Example 1 was used for Steps A–E, wherein the ketone used in Step E was N-t-butoxycarbonyl-4-piperidone. Step F was then carried out to make Compound G.

Step F: Compound F (0.87 g, 1.956 mmol) was dissolved in $CH_2Cl_2$ (5 ml) followed by addition of TFA (5 ml). The mixture was stirred at room temperature for 1 hr, and then evaporated. The residue was dissolved in $CH_2Cl_2$ (100 ml), washed with 1N NaOH solution, dried over $NaHCO_3$, and evaporated to give compound G (0.667 g, 98%).

EXAMPLE 4

Synthesis of Compound No. 8

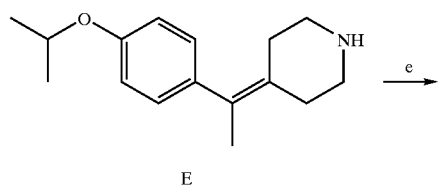

E

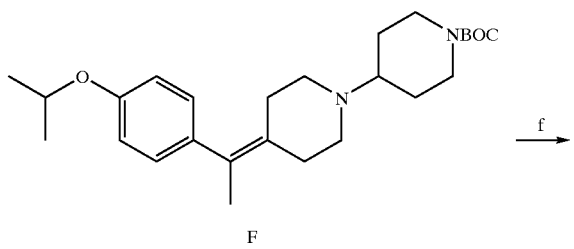

F

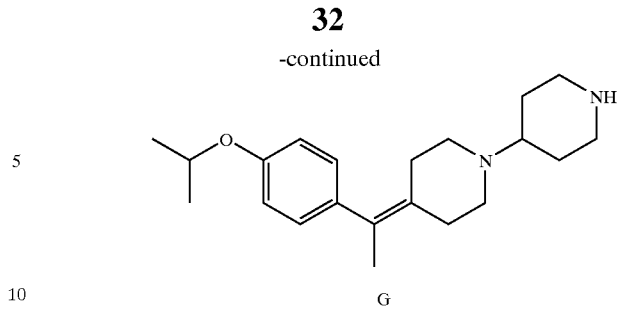

G

The same procedure as described in Example 3 was used except that 2-propanol was substituted for 2-propanethiol in Step B.

EXAMPLE 5

Synthesis of Compound Nos. 3, 4, 6, 11, 12, 16, 17, 23, 24, 27, 28, 37 and 49

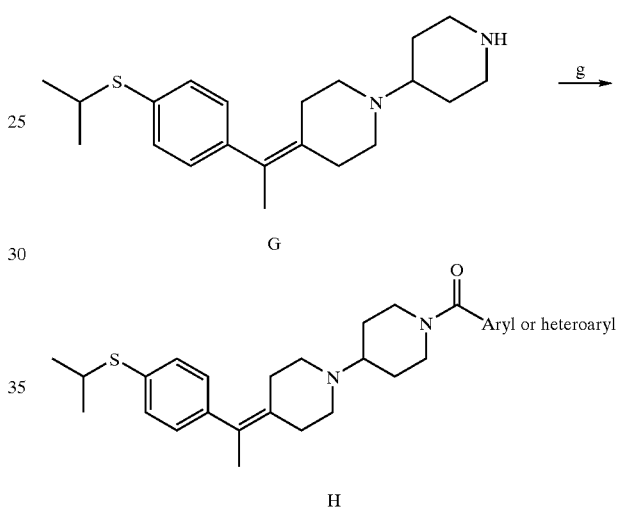

The same procedure as described in Example 3 was used for Steps A–F. Step G was then carried out to make Compound H.

G: General Procedure: After compound G (100 mg, 0.29 mmol) was dissolved in $CH_2Cl_2$ (5 ml), the corresponding acid (1.5 equiv.), EDCl (200 mg, 1 mmol), DMAP (5 mg) were added. The reaction mixture was stirred at room temperature under $N_2$ overnight. The product amide (Compound H) was separated by preparative TLC (7% MeOH in $CH_2Cl_2$).

EXAMPLE 6

Synthesis of Compound Nos. 1, 2, 10, 42, 43, 44 and 63

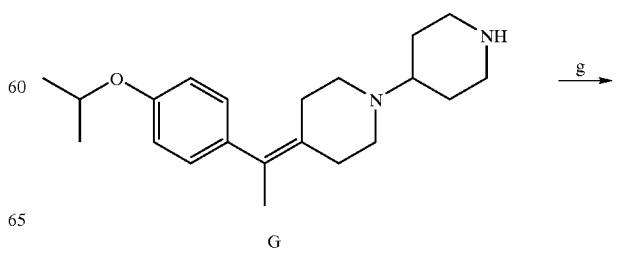

G

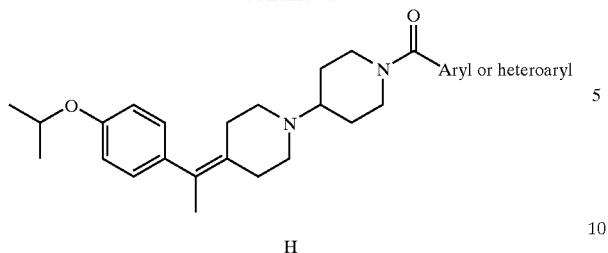

The same procedure as described in Example 5 was used except that 2-propanol was substituted for 2-propanethiol in Step B.

EXAMPLE 7

Synthesis of Compound Nos. 5,13–15,18–22, 25–26, 29–36, 38, 39 54, 55, 58, 59, and 64

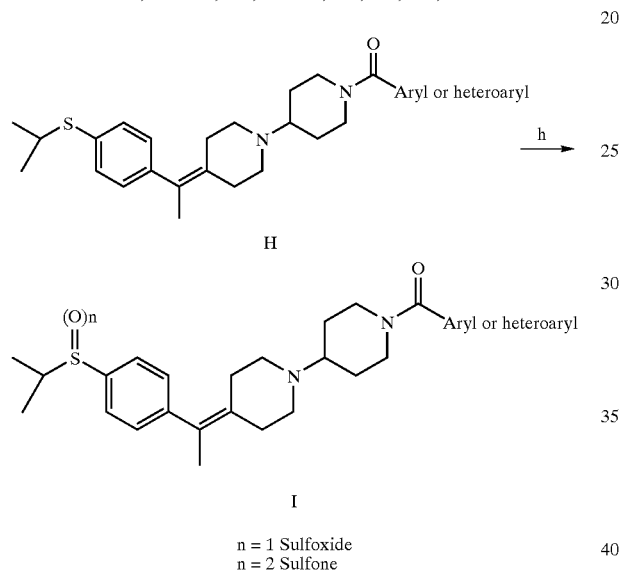

n = 1 Sulfoxide
n = 2 Sulfone

The same procedure as described in Example 5 was used for Steps A–G. Step H was then carried out to make Compound I.

H: The prepared amide in step G (100 mg, 0.207 mmol) was dissolved in acetic acid (4 ml) followed by addition of sodium perborate tetrahydrate (70 mg, 0.456 mmol, 2.2 equiv.). The reaction mixture was stirred at room temperature overnight, then quenched with 1N NaOH solution (50 ml). The mixture was extracted with $CH_2Cl_2$ (2×50 ml). The combined organic phase was dried over $NaHCO_3$ and evaporated. Sulfoxide and Sulfone were separated by preparative TLC (7%MeOH in $CH_2Cl_2$).

EXAMPLE 8

Synthesis of Compound Nos. 45–46, 50–53, 56, 57, 63, 66, 67 and 68

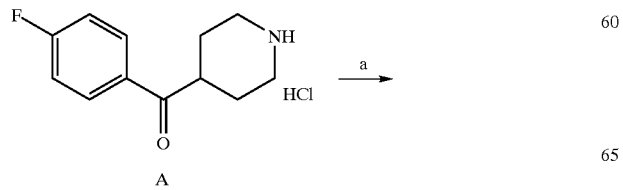

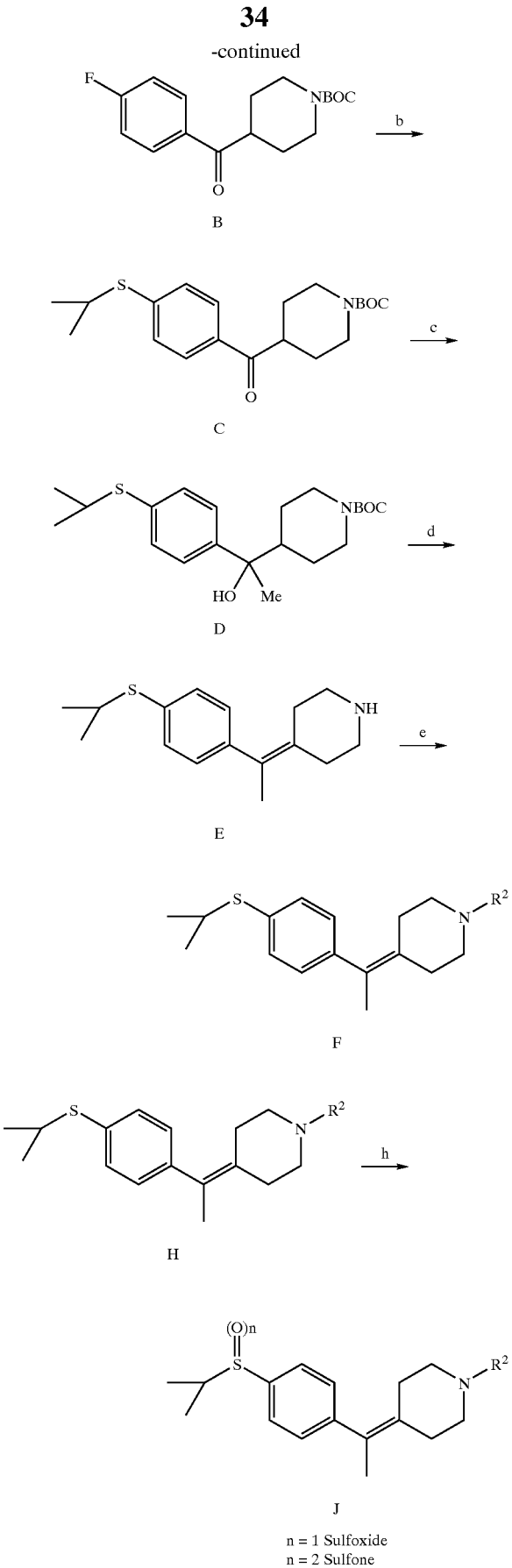

n = 1 Sulfoxide
n = 2 Sulfone

The same procedure as described in Examples 1 and 3 was used for Steps A–F. Step H as described in Example 7 was then carried out to make compound J. The ketones used in step E to make Compound Nos. 45–46; 50–51; 52–53, 63, and 66–68; and 56–57 were, respectively, cyclohexanol, 4-methylcyclohexanol; 3-methylcyclohexanol; and 4-isopropylcyclohexanol.

EXAMPLE 9

Synthesis of Compound Nos. 69–70

The same procedure as described in Example 8 was carried out to make compound J except that 4-methoxyphenylthioi was substituted for 2-propanethiol in step B. The ketone used in step E to make Compound Nos. 69–70 was 3-methylcyclohexanol.

EXAMPLE 10

Synthesis of Compound No. 71

The same procedure as described in Example 8 was carried out to make compound J except that 3-chlorophenylthiol was substituted for 2-propanethiol in step B. The ketone used in step E to make Compound Nos. 69–70 was 3-methylcyclohexanol.

The above reactions may be followed if necessary or desired by one or more of the following steps; (a) removing any protective groups from the compound so produced; (b) converting the compound so-produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequences, those skilled in the art will be able to select starting materials needed to produce any compound in accordance with formula I.

In the above processes it is sometimes desirable and/or necessary to protect certain groups during the reactions. Conventional protecting groups, familiar to those skilled in the art, are operable. After the reaction or reactions, the protecting groups may be removed by standard procedures.

Using the appropriate starting materials in the procedures described above or modifications of those procedures well known to those skilled in the art, the compounds shown in the following Table of Compounds can be prepared.

| Compound Number | STRUCTURE | HRMS caculated | HRMS observed |
|---|---|---|---|
| 1 | 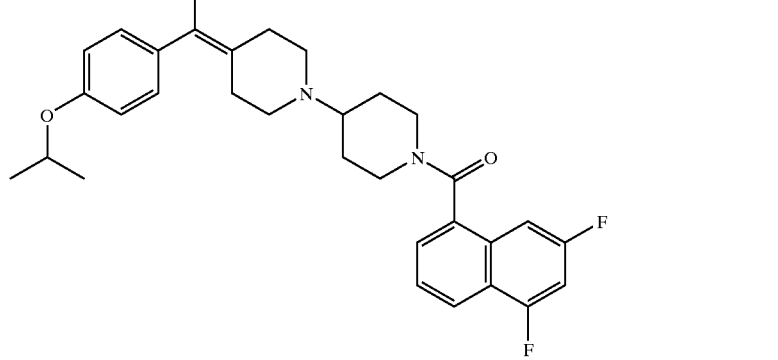 | 519.2823 | 519.2819 |
| 2 | 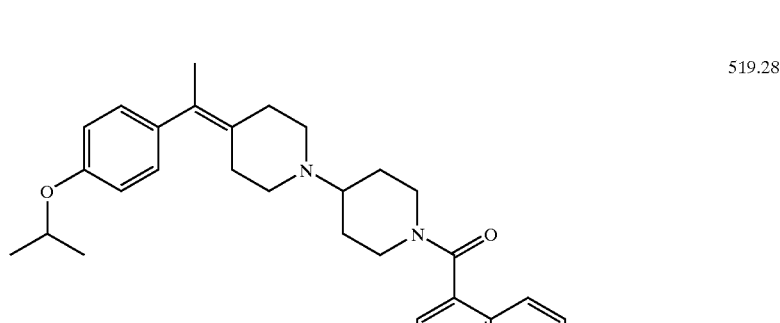 | 519.2823 | 519.2811 |

TABLE OF COMPOUNDS

| Compound Number | STRUCTURE | HRMS caculated | HRMS observed |
|---|---|---|---|
| 3 | 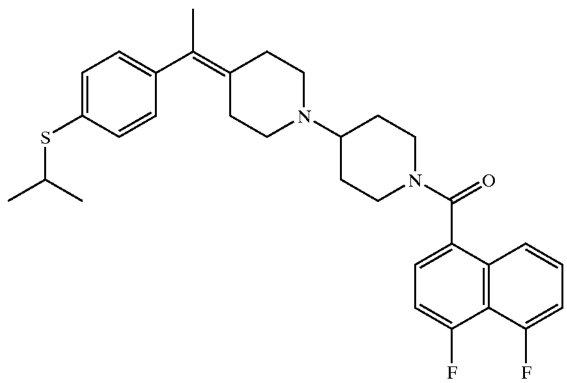 | 535.2608 | 535.2595 |
| 4 | 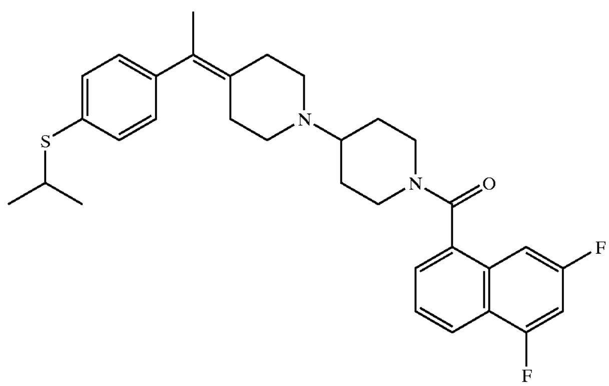 | 535.2603 | 535.2595 |
| 5 | 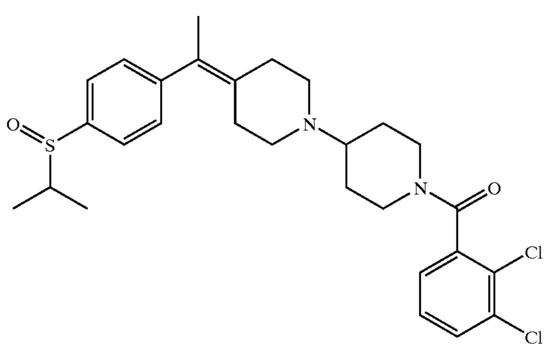 | 533.1796 | 533.1795 |
| 6 | 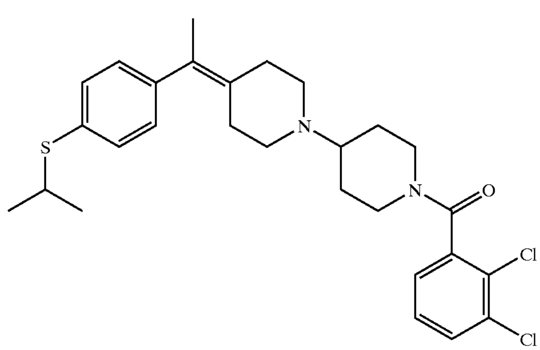 | 517.1847 | 517.1853 |

-continued
TABLE OF COMPOUNDS
| Compound Number | STRUCTURE | HRMS caculated | HRMS observed |
|---|---|---|---|
| 7 | 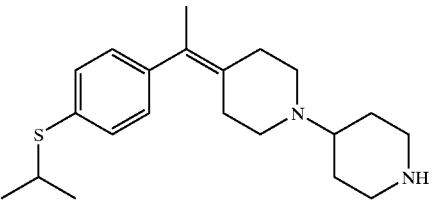 | 345.2364 | 345.2367 |
| 8 | 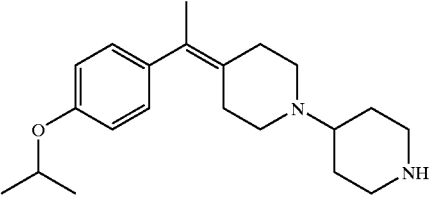 | 329.2593 | 329.259 |
| 9 | 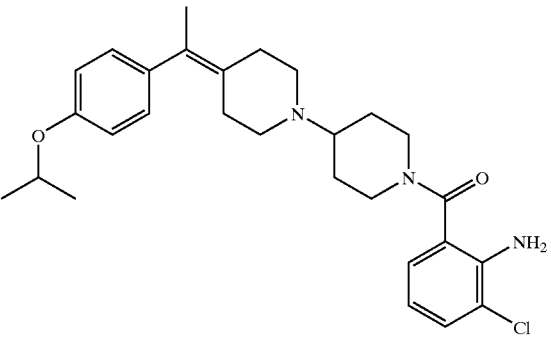 | 482.2574 | 482.2575 |
| 10 | 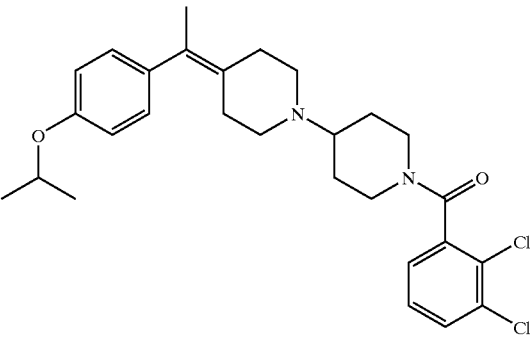 | 501.2076 | 501.2066 |
| 11 | 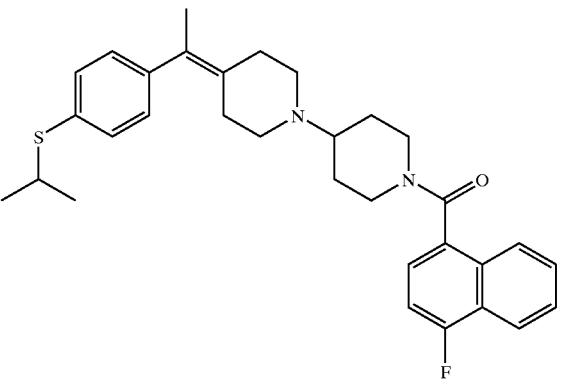 | 517.2689 | 517.2696 |

-continued
TABLE OF COMPOUNDS
| Compound Number | STRUCTURE | HRMS caculated | HRMS observed |
|---|---|---|---|
| 12 | 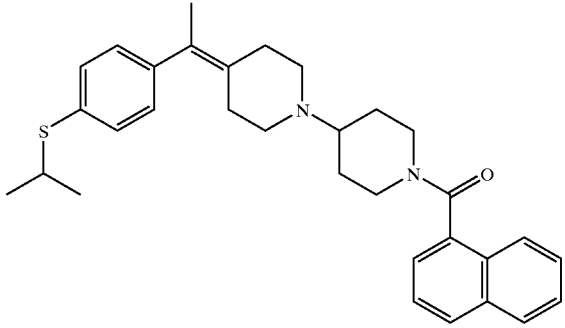 | 499.2783 | 499.2784 |
| 13 | 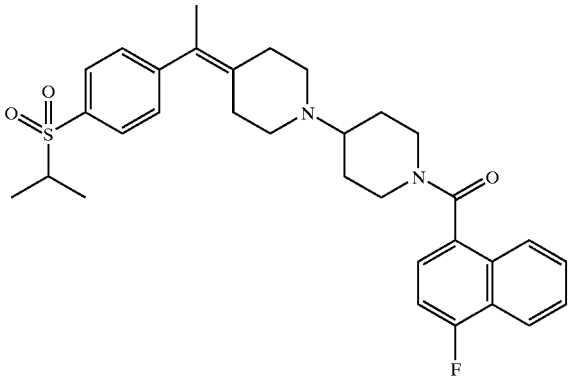 | 549.2587 | 549.2579 |
| 14 | 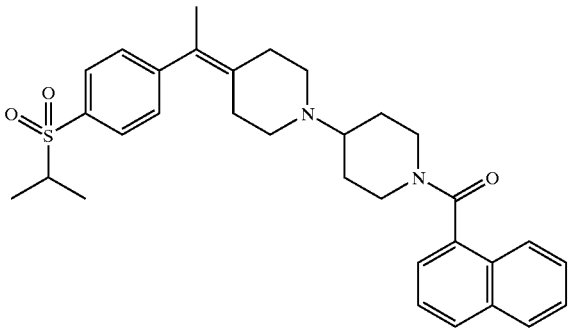 | 531.2681 | 531.2692 |
| 15 | 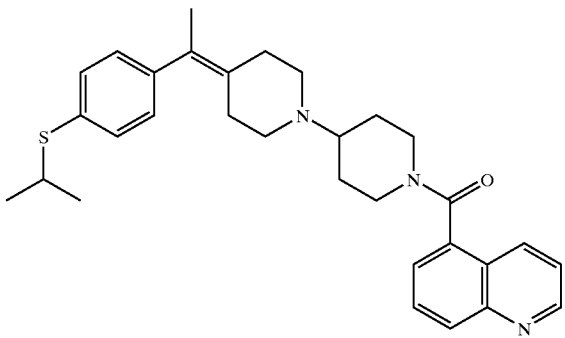 | 500.2736 | 500.2732 |

-continued

TABLE OF COMPOUNDS

| Compound Number | STRUCTURE | HRMS caculated | HRMS observed |
|---|---|---|---|
| 16 | 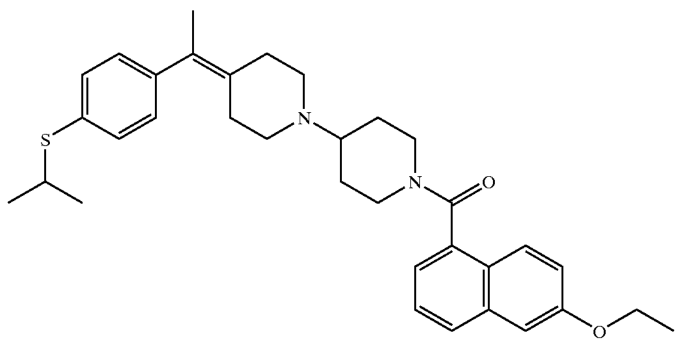 | 543.3045 | 543.3039 |
| 17 | 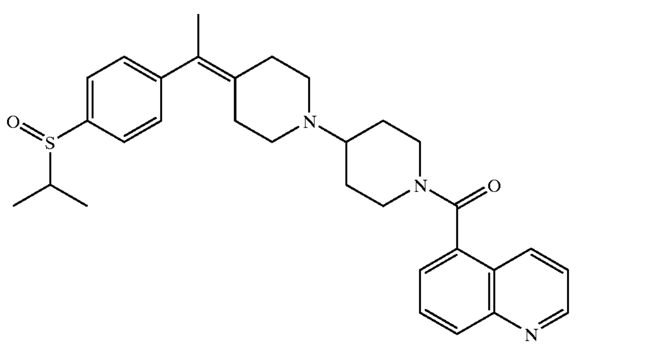 | 516.2685 | 516.2693 |
| 18 | 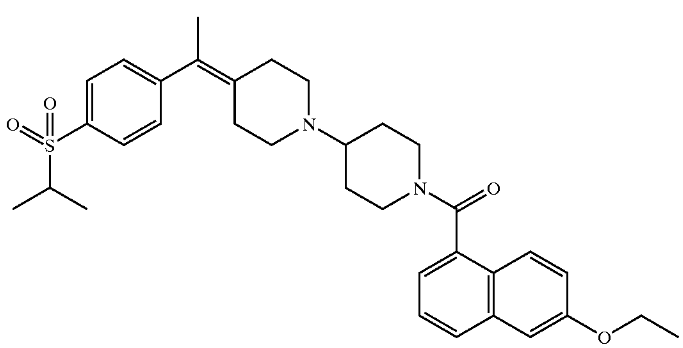 | 575.2944 | 575.2933 |
| 19 | 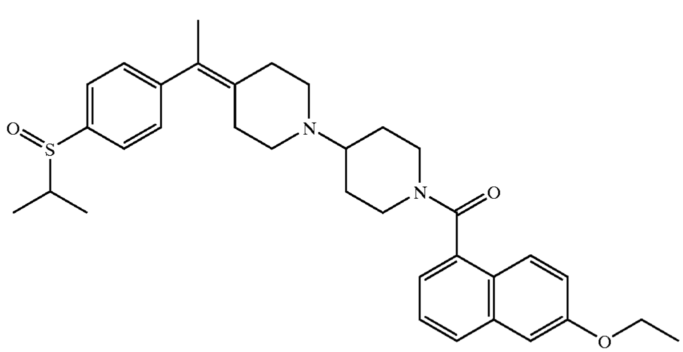 | 559.2994 | 559.2991 |

-continued

TABLE OF COMPOUNDS

| Compound Number | STRUCTURE | HRMS caculated | HRMS observed |
|---|---|---|---|
| 20 | 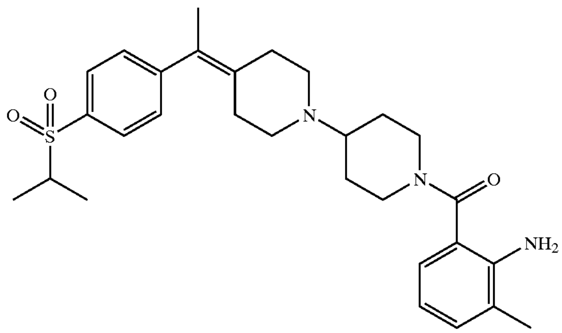 | 510.279 | 510.2774 |
| 21 | 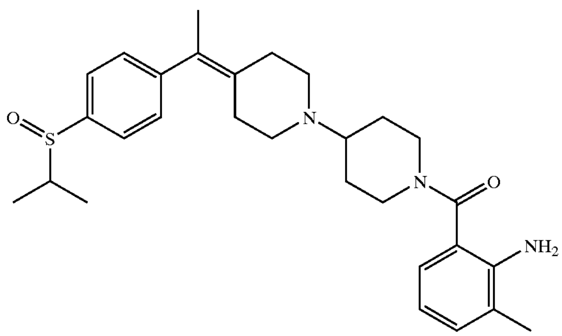 | 494.2841 | 494.2842 |
| 22 | 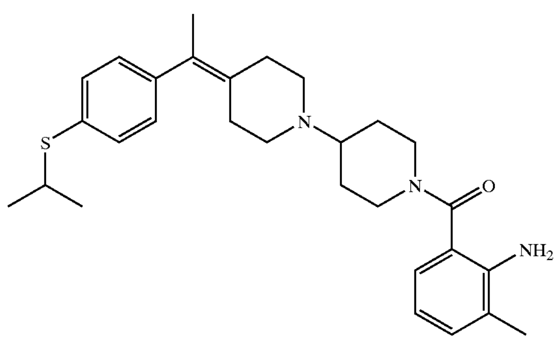 | 478.2892 | 478.2918 |
| 23 | 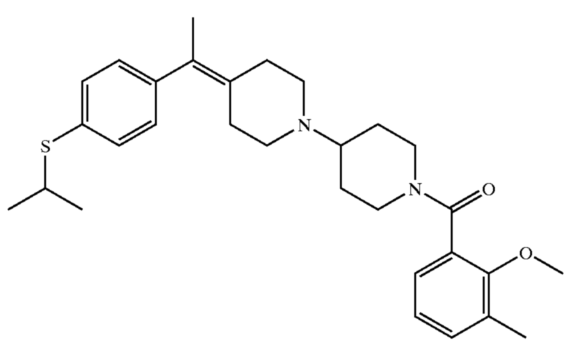 | 493.2889 | 493.2875 |

TABLE OF COMPOUNDS -continued

| Compound Number | STRUCTURE | HRMS caculated | HRMS observed |
|---|---|---|---|
| 24 | 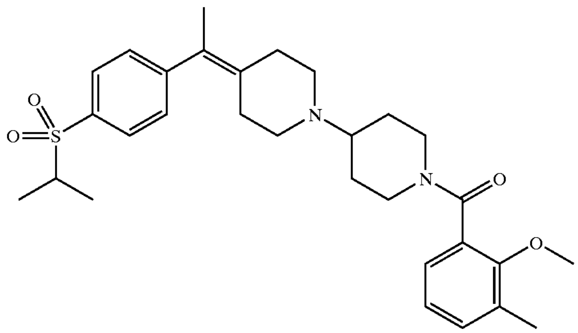 | 525.2785 | 525.2787 |
| 25 | 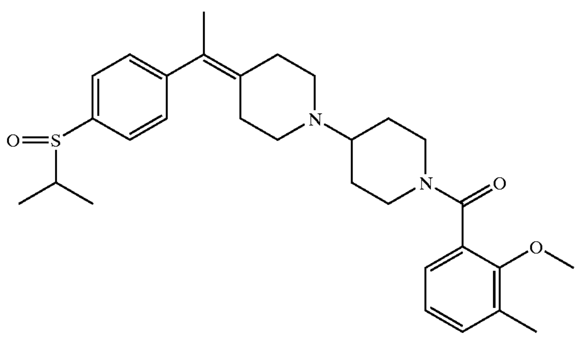 | 509.2838 | 509.2832 |
| 26 | 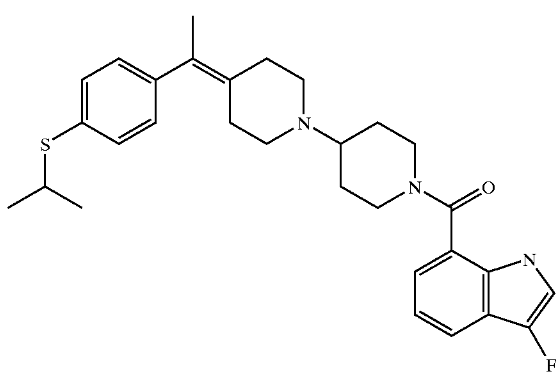 | 506.2641 | 506.2648 |
| 27 | 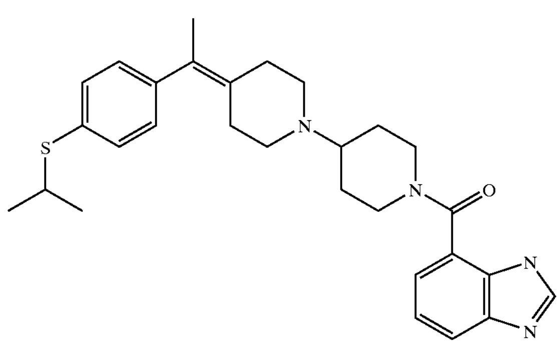 | 489.2688 | 489.2682 |

-continued

TABLE OF COMPOUNDS

| Compound Number | STRUCTURE | HRMS caculated | HRMS observed |
|---|---|---|---|
| 28 | 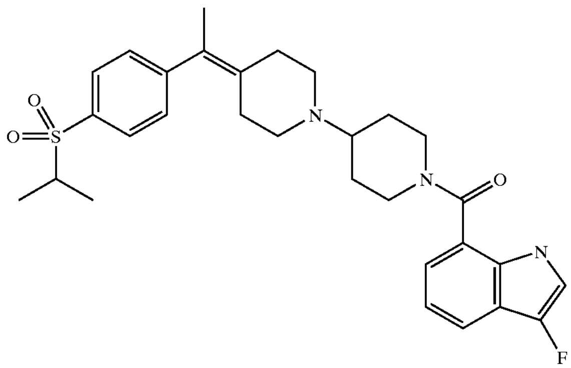 | 538.254 | 538.2555 |
| 29 | 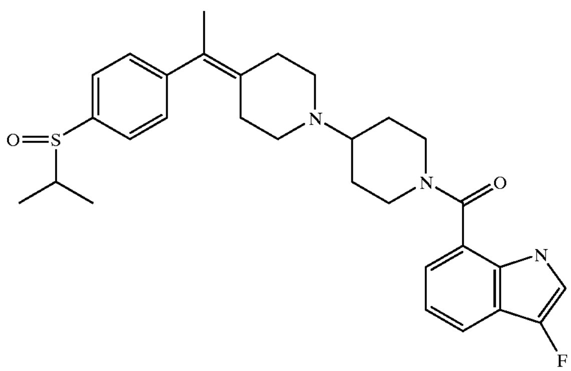 | 522.2591 | 522.2604 |
| 30 | 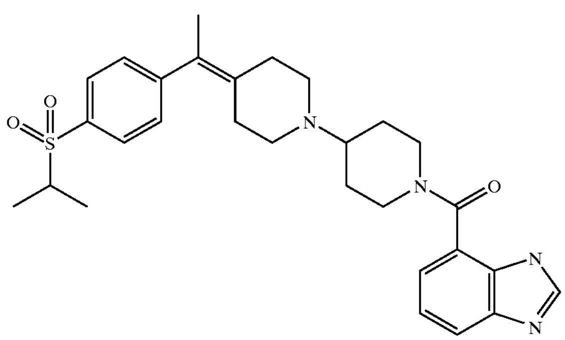 | 521.2586 | 521.2561 |
| 31 | 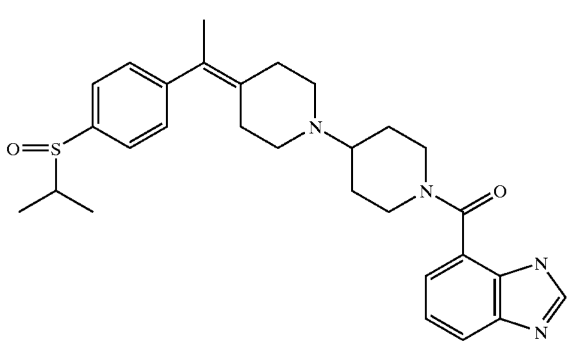 | 505.2637 | 505.2638 |

-continued
TABLE OF COMPOUNDS
| Compound Number | STRUCTURE | HRMS caculated | HRMS observed |
|---|---|---|---|
| 32 | 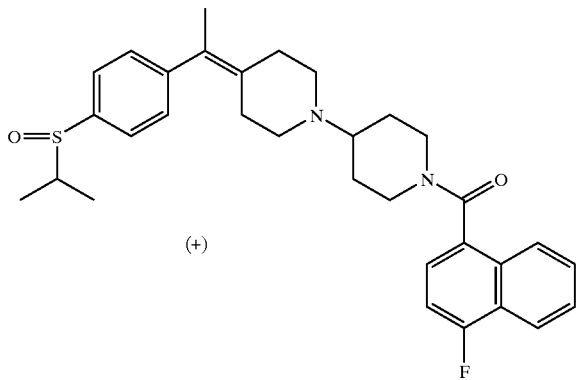 (+) | 533.2638 | 533.2642 |
| 33 | 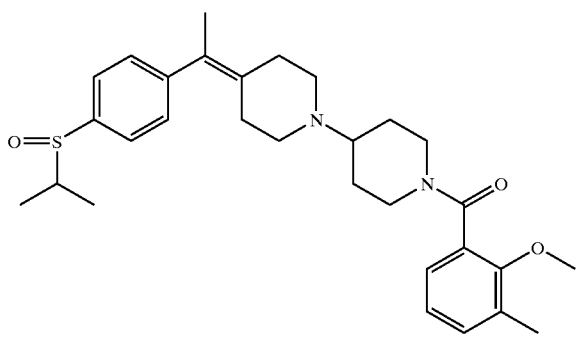 | 509.2838 | 509.2837 |
| 34 | 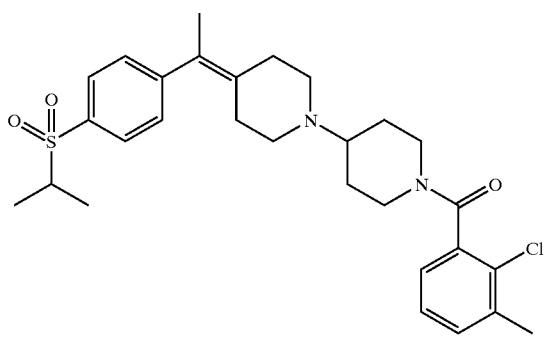 | 529.2292 | 529.2302 |
| 35 | 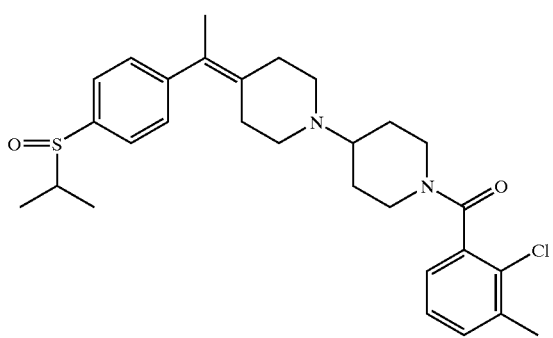 | 513.2343 | 513.235 |

-continued

TABLE OF COMPOUNDS

| Compound Number | STRUCTURE | HRMS caculated | HRMS observed |
|---|---|---|---|
| 36 | 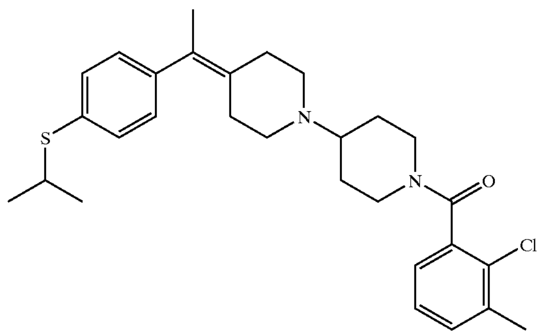 | 497.2393 | 497.239 |
| 37 | (+)Enantiomer | 494.2841 | 494.2847 |
| 38 | (-)Enantiomer | 494.2841 | 494.2832 |
| 39 | 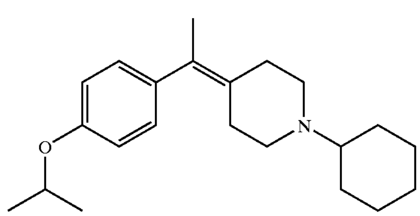 | 328.264 | 328.2636 |
| 40 | 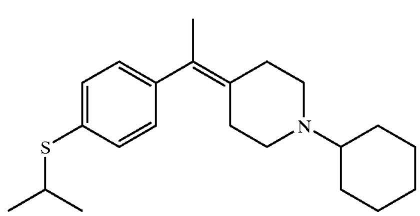 | 344.2412 | 344.2415 |

-continued

TABLE OF COMPOUNDS

| Compound Number | STRUCTURE | HRMS caculated | HRMS observed |
|---|---|---|---|
| 41 | 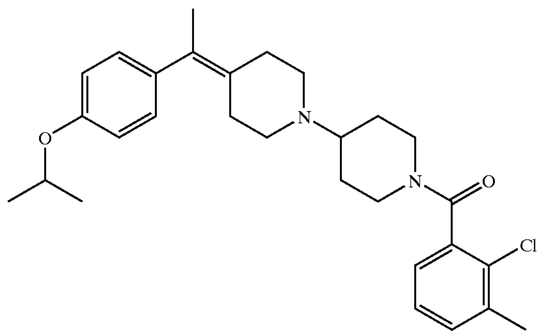 | 481.2622 | 481.2626 |
| 42 | 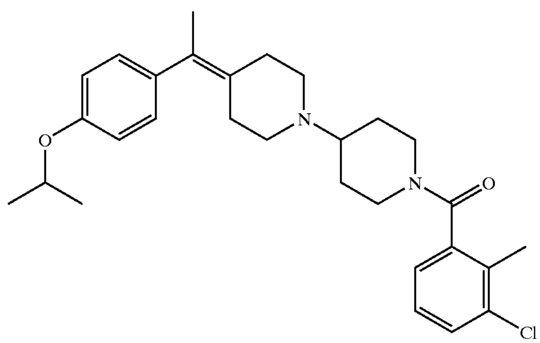 | 481.2622 | 481.2623 |
| 43 | 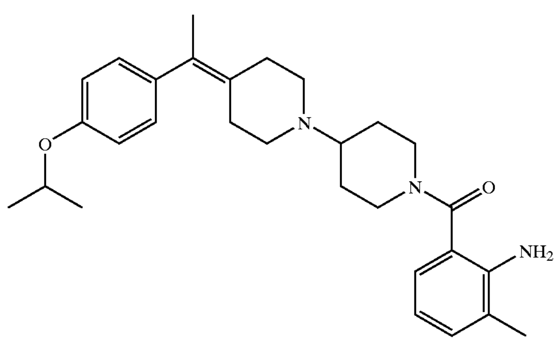 | 462.3121 | 462.3117 |
| 44 | 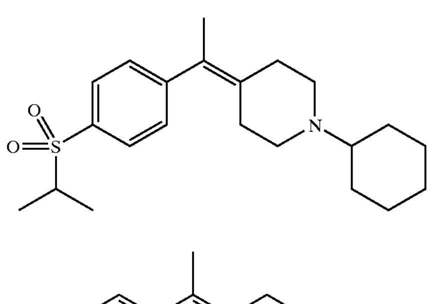 | 376.231 | 376.2321 |
| 45 | 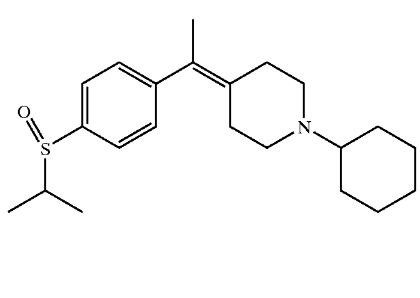 | 360.2361 | 360.2357 |

TABLE OF COMPOUNDS

| Compound Number | STRUCTURE | HRMS caculated | HRMS observed |
|---|---|---|---|
| 46 | 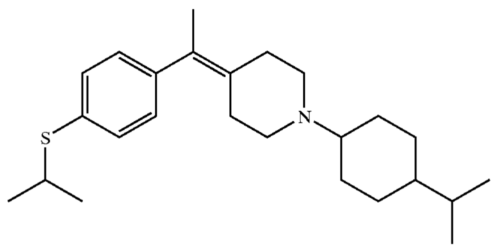 | 386.2881 | 386.2873 |
| 47 | 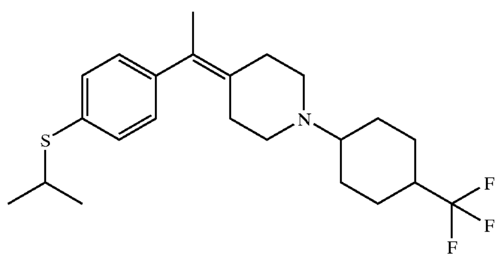 | 412.2286 | 412.2301 |
| 48 | 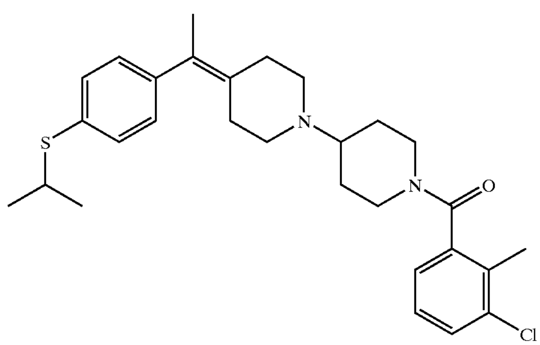 | 497.2393 | 497.24 |
| 49 | 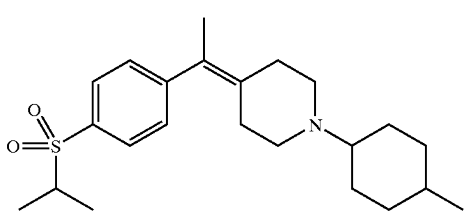 | 390.2467 | 390.2451 |
| 50 | 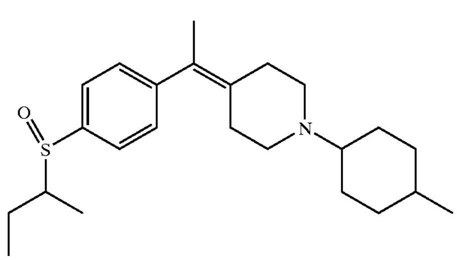 | 374.2518 | 374.2506 |

-continued

TABLE OF COMPOUNDS

| Compound Number | STRUCTURE | HRMS caculated | HRMS observed |
|---|---|---|---|
| 51 | 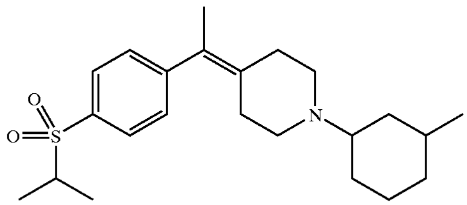 | 390.2467 | 390.2454 |
| 52 | 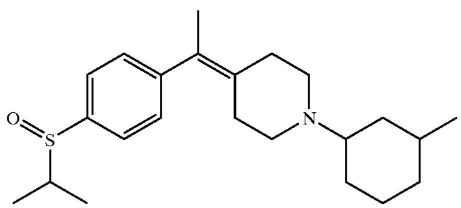 | 374.2518 | 374.2511 |
| 53 | 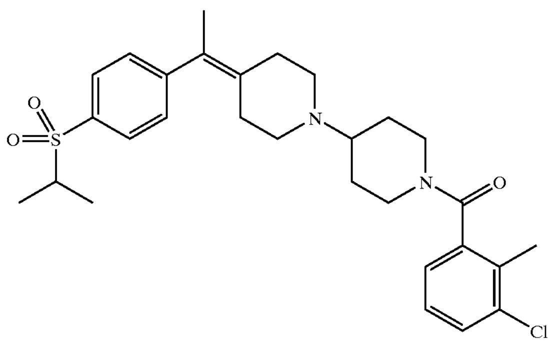 | 529.2292 | 529.2286 |
| 54 | 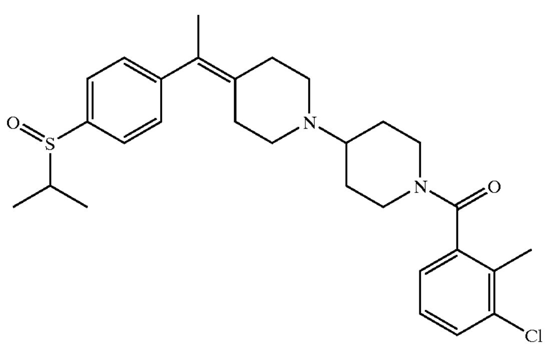 | 513.2343 | 513.2352 |
| 55 | 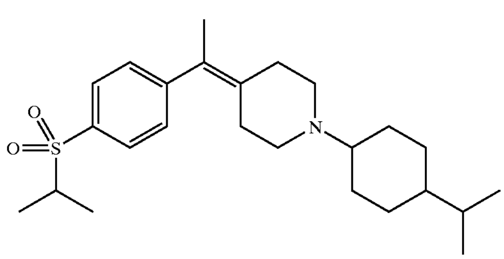 | 418.278 | 418.2777 |

-continued
TABLE OF COMPOUNDS
| Compound Number | STRUCTURE | HRMS caculated | HRMS observed |
|---|---|---|---|
| 56 | 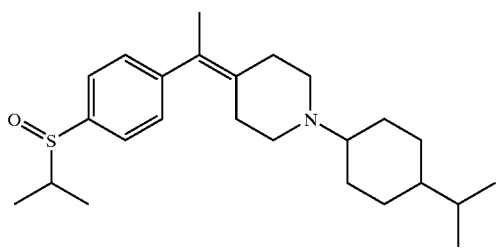 | 402.2831 | 402.2833 |
| 57 | 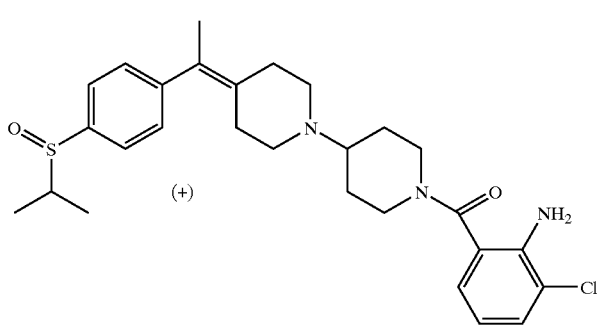 (+) | 514.2295 | 514.2291 |
| 58 | 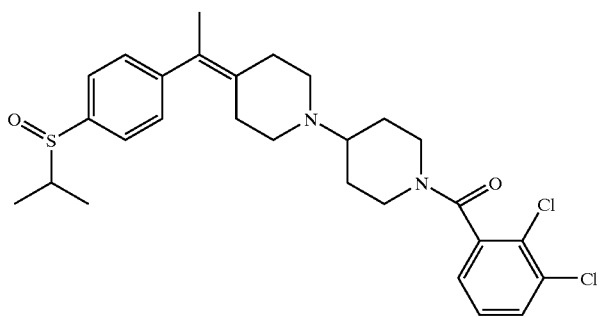 | 535.1767 | 535.1772 |
| 59 | 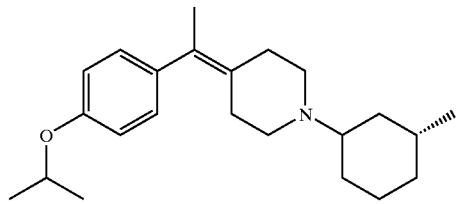 | 342.2797 | 342.2781 |
| 60 | 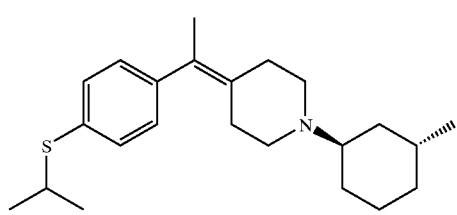 | 358.2568 | 358.2558 |

-continued

TABLE OF COMPOUNDS

| Compound Number | STRUCTURE | HRMS caculated | HRMS observed |
|---|---|---|---|
| 61 | 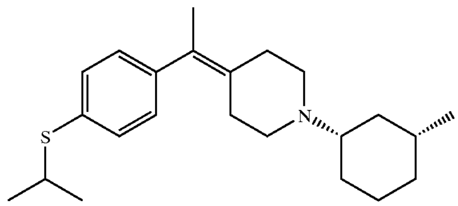 | 358.2568 | 358.2571 |
| 62 | 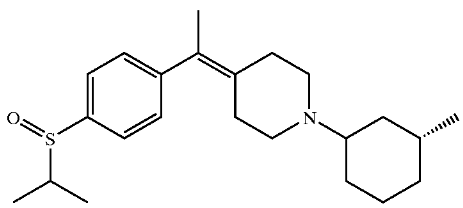 | 374.2518 | 374.252 |
| 63 | (+) | 513.2343 | 513.2338 |
| 64 | (−) | 503.2232 | 503.2233 |
| 65 | 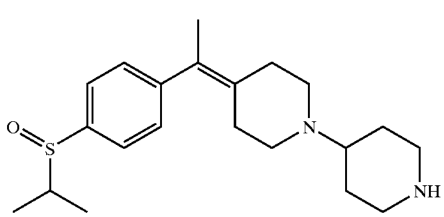 | 361.2314 | 361.2318 |

-continued

TABLE OF COMPOUNDS

| Compound Number | STRUCTURE | HRMS caculated | HRMS observed |
|---|---|---|---|
| 66 | 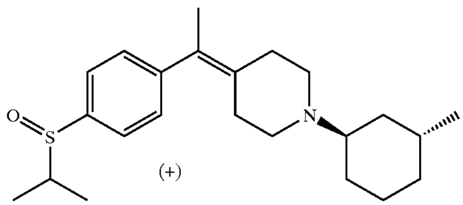 | 374.2518 | 374.2511 |
| 67 | 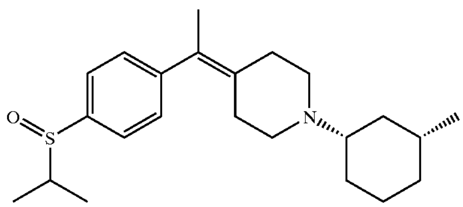 | 374.2518 | 374.2516 |
| 68 | 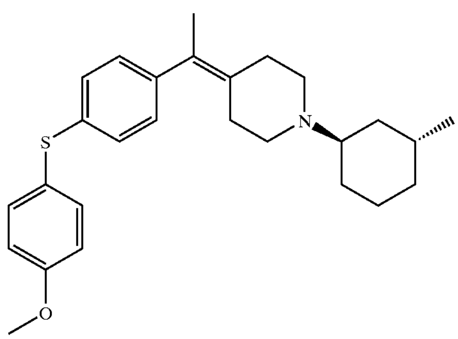 | 421.2439 | 421.2437 |
| 69 | 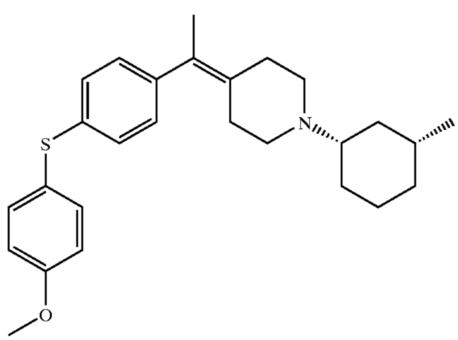 | 422.2518 | 422.2523 |
| 70 | 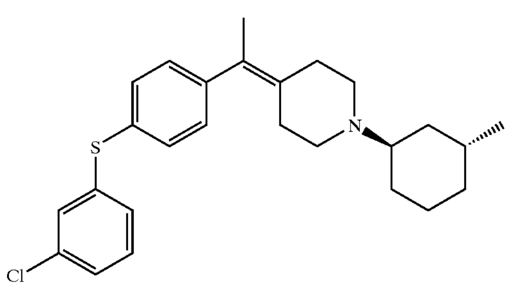 | 426.2022 | 426.2014 |

The compounds of formula I display pharmacological activity in test procedures designated to indicate M1 and M2 muscarinic antagonist activity. The compounds are non-toxic at pharmaceutically therapeutic doses. Following are descriptions of the test procedures.

Muscarinic Binding Activity

The compound of interest is tested for its ability to inhibit binding to the cloned human M1, M2, M3, M4 and M5 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homgenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 µg of protein assay for the M1, M2, and M4 containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 µM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, 1985). Affinity values ($K_i$) were then determined using the following formula (Cheng and Prusoff, 1973);

$$K_i = \frac{IC_{50}}{1 + \left[\frac{\text{concentration of radioligand}}{\text{affinity}(K_D) \text{ of radioligand}}\right]}$$

Hence, a lower value of $K_i$ indicates greater binding affinity. To determine the degree of selectivity of a compound for binding to a particular muscarinic receptor, the $K_i$ value of a first muscarinic receptor is divided by the $K_i$ value of another muscarinic receptor. For example, when the $K_i$ value of the M1 receptors is divided by the $K_i$ value of the M2 receptors, a higher ratio indicates a greater selectivity for binding to the M2 muscarinic receptor.

For the compounds appearing in the TABLE OF COMPOUNDS, the range of muscarinic antagonistic activity for the M2 receptor was found to be from about 0.295 nM to about 168.15 nM.

While the present invention has been described in conjunction with the specific embodiments set forth above, many alternatives, modifications and other variations threof will be apparent to those of ordinary skill in the art. All such altertnatives, modifications and variatioins are intended to fall within the spirit and scope of the present invention.

What is claimed:

1. A compound represented by the structural formula:

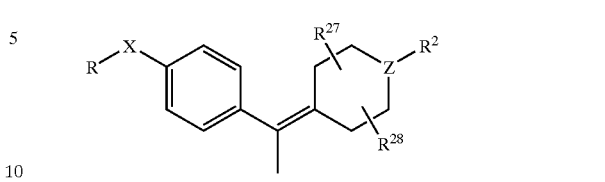

I or a pharmaceutically acceptable salt or solvate of said compound, wherein:

Z is N;

X is —O—, —S—, —SO—, —S(O)$_2$—, —C(O)—, or —C(S);

R is 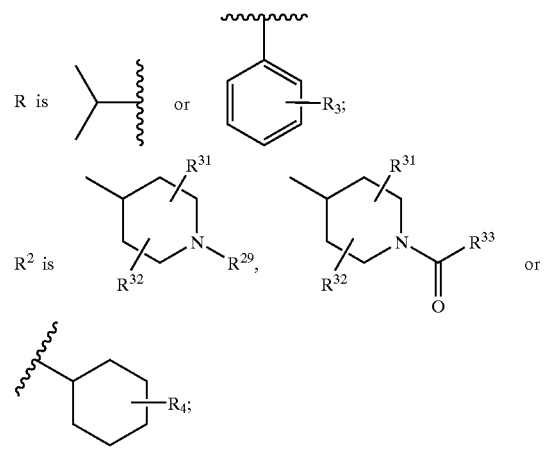

$R^3$ is 1 to 5 substituents which can be the same or different, each said substituent being either alkoxy or halo;

$R^4$ ;

$R^{27}$ is hydrogen or 1 or 2 substituents which can be the same or different, each said substituent being independently selected from the group consisting of alkyl, hydroxyalkyl, arylalkyl, aminoalkyl, haloalkyl, alkylthio, alkylthioalkylenyl, carboxyalkyl, imidazolyalkyl and indolylalkyl;

$R^{28}$ is hydrogen or 1 or 2 substituents which can be the same or different, each said substituent being independently selected from the group consisting of alkyl, hydroxyalkyl, arylalkyl, aminoalkyl, haloalkyl, alkylthio, alkylthioalkylenyl, carboxyalkyl, imidazolyalkyl and indolylalkyl; or $R^{27}$ and $R^{28}$ can be joined together to form an alkylene group;

$R^{29}$ is hydrogen, alkyl, —C(O)-alkyl, —C(O)-cycloalkyl, alkoxycarbonyl, aminocarbonyl, aryloxycarbonyl, alkylaminocarbonyl, alkylsulfonyl, arysulfonyl or —SO$_2$—NH—R$^{35}$;

$R^{31}$ is hydrogen or 1 or 2 substituents which can be the same or different, each said substituent being independently selected from the group consisting of alkyl, aryl, cycloalkyl, hydroxyalkyl, aminoalkyl, hydroxy, —N(R$^{35}$)$_2$, —O-acyl, —N(R$^{35}$)acyl, —OC(O)OR$^{35}$ and —OC(O)N(R$^{35}$)$_2$;

$R^{32}$ is hydrogen or 1 or 2 substituents which can be the same or different, each said substituent being independently selected from the group consisting of alkyl, aryl, cycloalkyl, hydroxyalkyl, aminoalkyl, hydroxy, —N(R$^{35}$)$_2$, —O-acyl, —N(R$^{35}$)acyl, —OC(O)OR$^{35}$ and —OC(O)N(R$^{35}$)$_2$, or R$^{31}$ and R$^{32}$ can be joined together to form the group —(CH$_2$)$_r$—, wherein r is 1, 2, 3, 4, 5 or 6; and R$^{35}$ is hydrogen, aryl or alkyl.

2. A compound as defined in claim 1 or a pharmaceutically acceptable salt or solvate thereof, wherein R$^2$ is

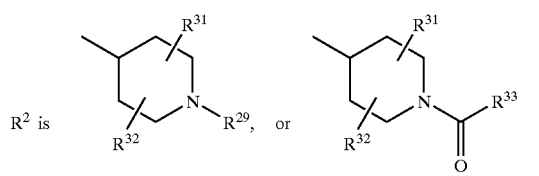

and

X is —O—, —S—, —SO— or —S(O)$_2$—.

3. A compound as defined in claim 1 selected from the group consisting of

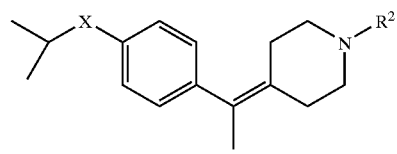

or a pharmaceutically acceptable salt or solvate of said compound, wherein R$^2$ and X are defined as follows:

| No. from table of compounds | R$^2$ | X |
|---|---|---|
| 1 | ![piperidine-naphthalene-diF] | O |
| 2 | ![piperidine-naphthalene-diF] | O |
| 3 | ![piperidine-naphthalene-diF] | S |
| 4 | ![piperidine-naphthalene-diF] | S |
| 5 | ![piperidine-dichlorophenyl] | SO |
| 6 | ![piperidine-dichlorophenyl] | S |
| 7 | ![piperidine-NH] | S |
| 8 | ![piperidine-NH] | O |

-continued
| No. from table of compounds | R² | X |
|---|---|---|
| 9 | 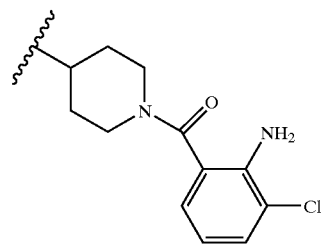 | O |
| 10 | 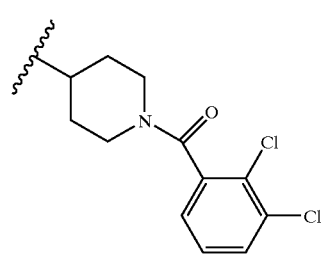 | O |
| 11 | 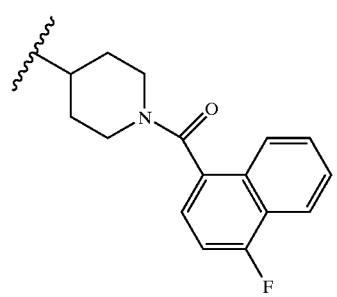 | S |
| 12 | 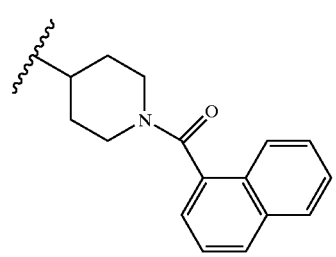 | S |
| 13 | 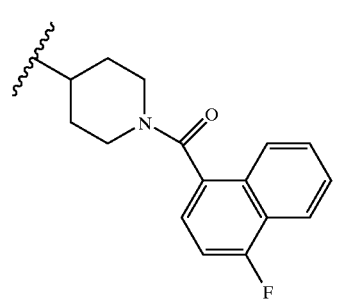 | SO₂ |
-continued
| No. from table of compounds | R² | X |
|---|---|---|
| 14 | 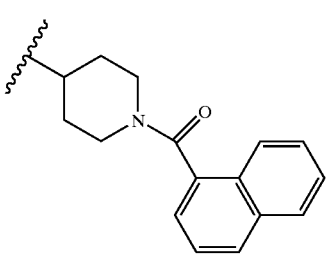 | SO₂ |
| 15 | 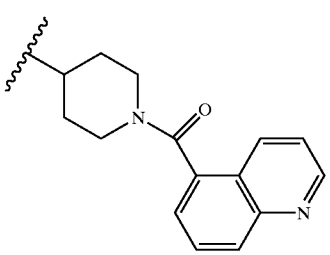 | S |
| 16 | 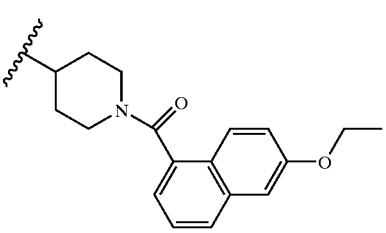 | S |
| 17 | 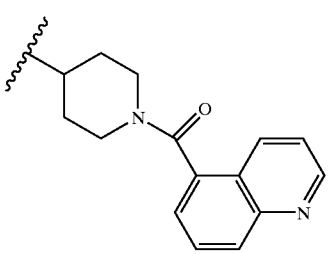 | SO |
| 18 | 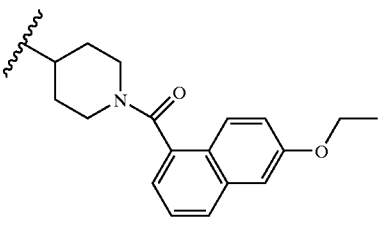 | SO₂ |
| 19 | 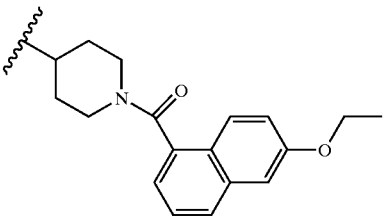 | SO |

-continued
| No. from table of compounds | R² | X |
|---|---|---|
| 20 | 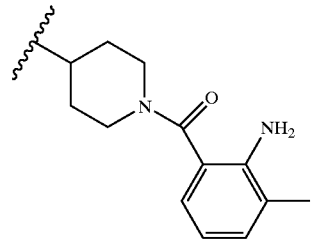 | SO₂ |
| 21 | 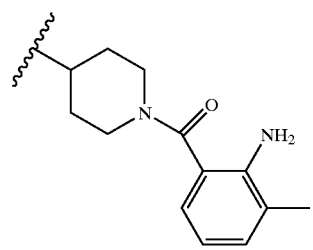 | SO |
| 22 | 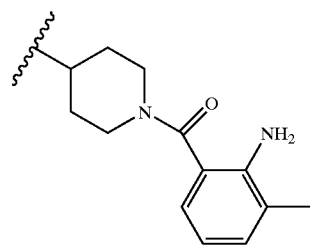 | S |
| 23 | 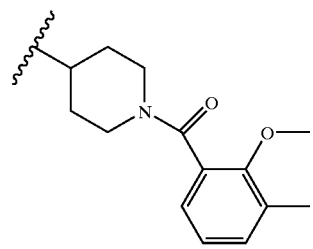 | S |
| 24 | 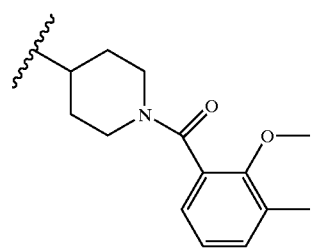 | SO₂ |
| 25 | 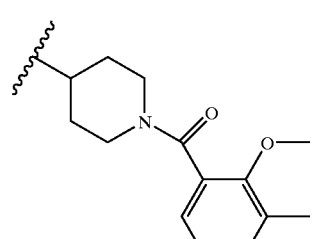 | SO |
-continued
| No. from table of compounds | R² | X |
|---|---|---|
| 26 | 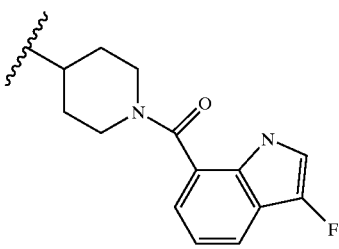 | S |
| 27 | 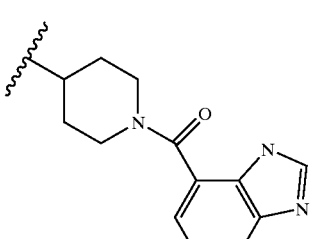 | S |
| 28 | 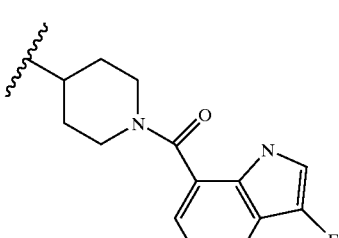 | SO₂ |
| 29 | 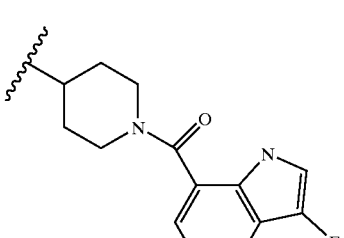 | SO |
| 30 | 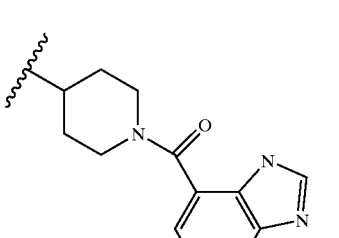 | SO₂ |
| 31 | 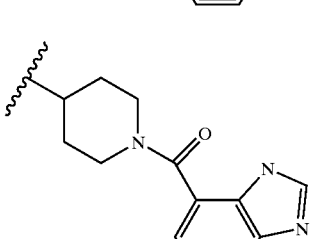 | SO |

-continued
| No. from table of compounds | R² | X |
|---|---|---|
| 32 | 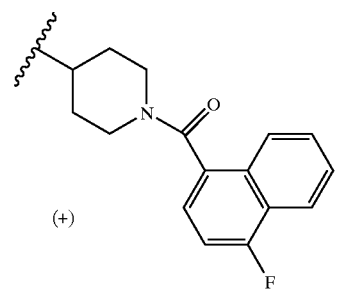 (+) | SO |
| 33 | 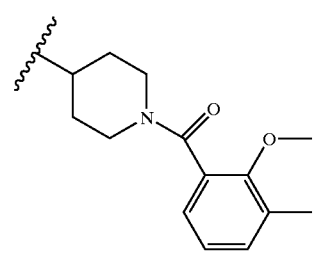 | SO |
| 34 | 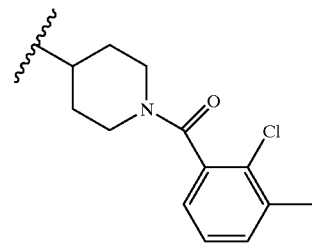 | SO₂ |
| 35 | 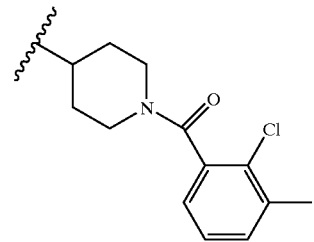 | SO |
| 36 | 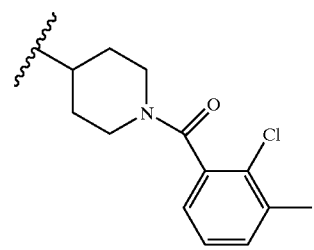 | S |
-continued
| No. from table of compounds | R² | X |
|---|---|---|
| 37 | 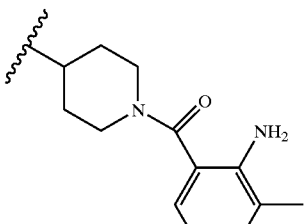 (+)Enantiomer | SO |
| 38 | (-)Enantiomer | SO |
| 41 | | O |
| 42 | | O |
| 43 | | O |

| No. from table of compounds | R² | X |
|---|---|---|
| 48 | 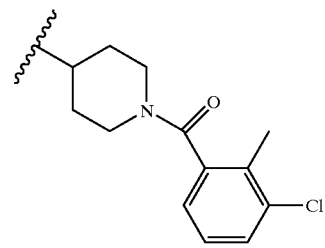 | S |
| 53 | 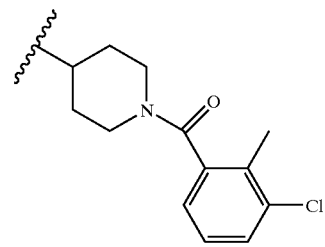 | SO₂ |
| 54 | 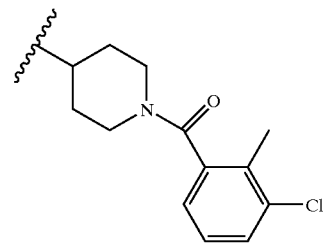 | SO |
| 57 | 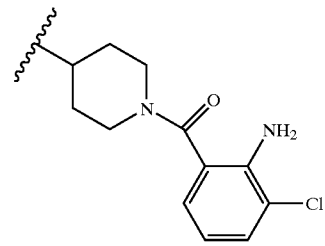 | SO |
| 58 | 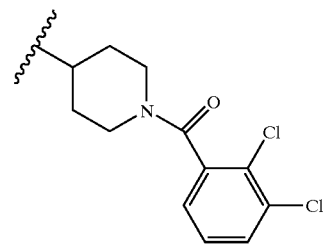 | SO |
| 63 | 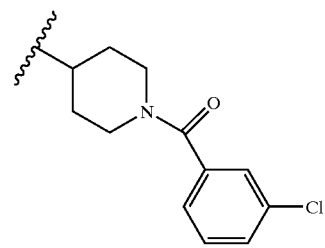 | SO |
| No. from table of compounds | R² | X |
|---|---|---|
| 64 | 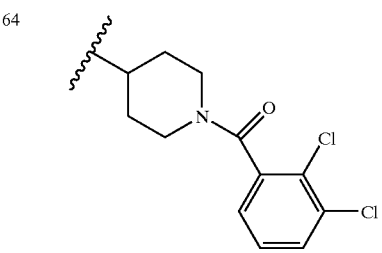 | O |
| 65 | 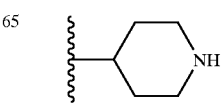 | SO. |
4. A compound according to claim 3, or a pharmaceutically acceptable salt or solvate of said compound, having the following formula:
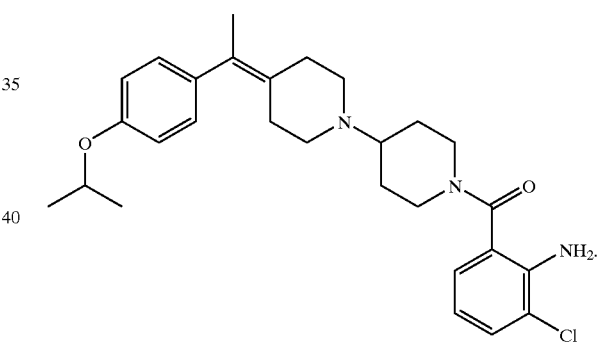
5. A compound according to claim 3, or a pharmaceutically acceptable salt or solvate of said compound, having the following formula:
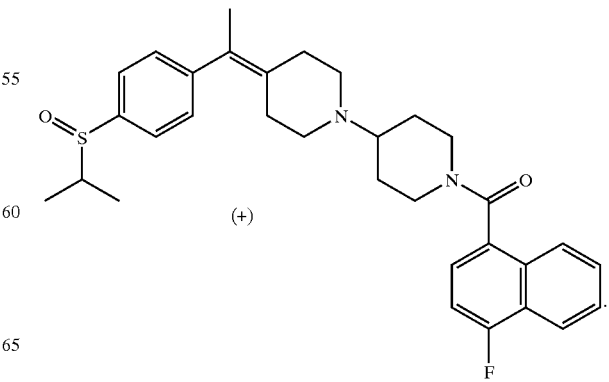

6. A compound according to claim 3, or a pharmaceutically acceptable salt or solvate of said compound, having the following formula:

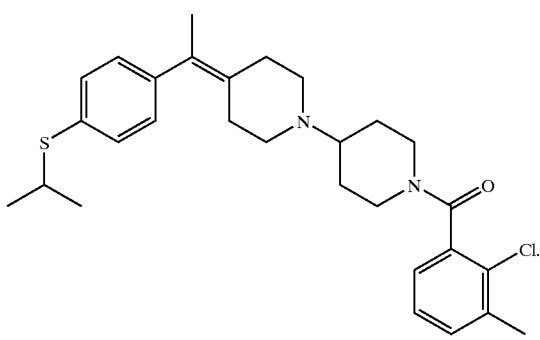

7. A compound according to claim 3, or a pharmaceutically acceptable salt or solvate of said compound, having the following formula:

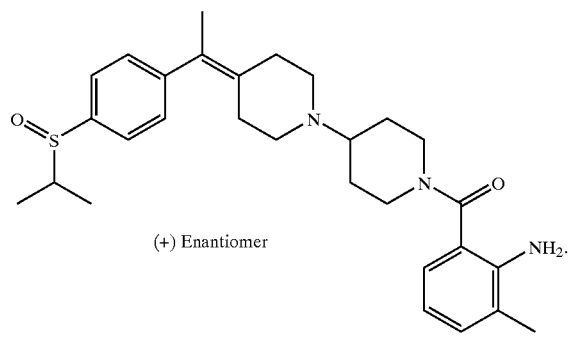

8. A compound according to claim 3, or a pharmaceutically acceptable salt or solvate of said compound, having the following formula:

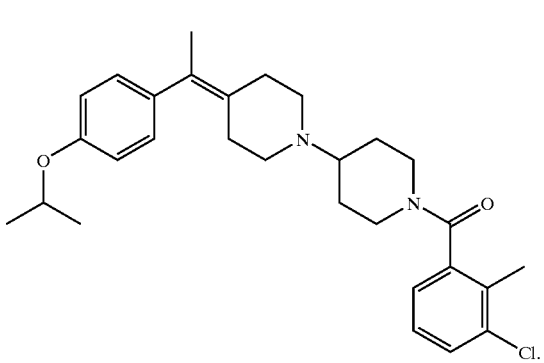

9. A compound according to claim 3, or a pharmaceutically acceptable salt or solvate of said compound, having the following formula:

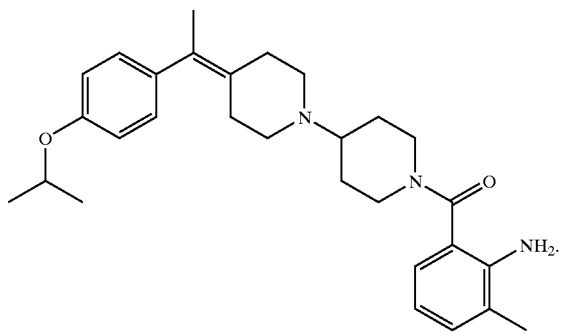

10. A compound according to claim 3, or a pharmaceutically acceptable salt or solvate of said compound, having the following formula:

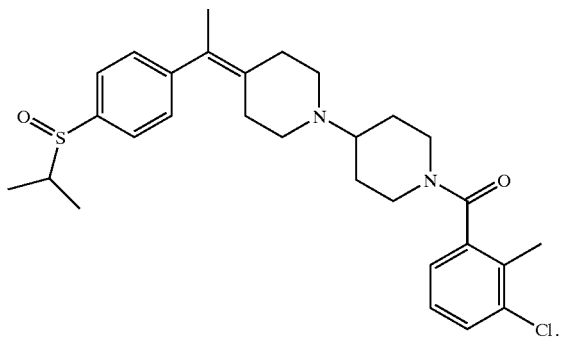

11. A compound according to claim 3, or a pharmaceutically acceptable salt or solvate of said compound, having the following formula:

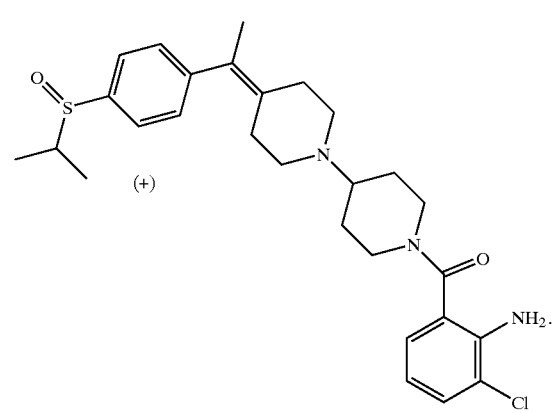

12. A compound according to claim 3, or a pharmaceutically acceptable salt or solvate of said compound, having the following formula:

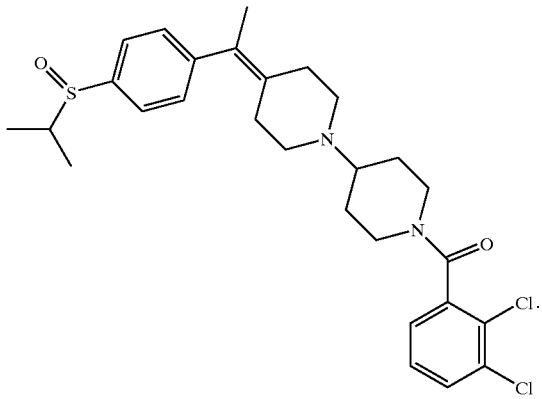

13. A compound according to claim 3, or a pharmaceutically acceptable salt or solvate of said compound, having the following formula:

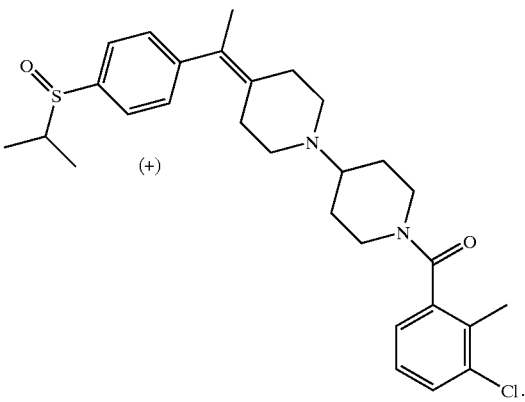

(+)

14. A pharmaceutical composition which comprises a therapeutically effective amount of at least one compound as defined in claim 1 in combination with a pharmaceutically acceptable carrier.

15. A method of making a pharmaceutical composition comprising mixing a therapeutically effective amount of at least one compound of claim 1 with a pharmaceutically acceptable carrier.

* * * * *

UNITED STATES PATENT AND TRADEMARK OFFICE
CERTIFICATE OF CORRECTION

PATENT NO.       : 6,831,089 B2
APPLICATION NO.  : 10/266505
DATED            : December 14, 2004
INVENTOR(S)      : Wang et al.

Page 1 of 1

It is certified that error appears in the above-identified patent and that said Letters Patent is hereby corrected as shown below:

In claim 1, column 68, lines 25-35, should read:

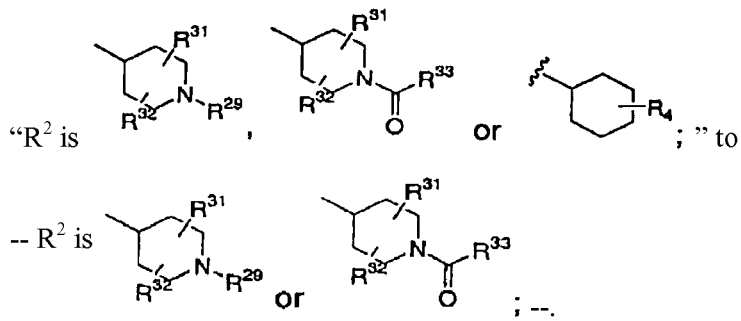

In claim 1, column 68, line 40, delete "$R^4$".

In claim 2, column 69, line 15, delete "$R^2$ is".

Signed and Sealed this

Tenth Day of June, 2008

JON W. DUDAS
*Director of the United States Patent and Trademark Office*